United States Patent
Tabary et al.

(10) Patent No.: US 11,130,950 B2
(45) Date of Patent: Sep. 28, 2021

(54) METHODS AND PHARMACEUTICAL COMPOSITIONS FOR THE TREATMENT OF CYSTIC FIBROSIS

(71) Applicants: INSERM (INSTITUT NATIONAL DE LA SANTE ET DE LA RECHERCHE MEDICALE), Paris (FR); UNIVERSITE PIERRE ET MARIE CURIE (PARIS 6), Paris (FR)

(72) Inventors: Olivier Tabary, Paris (FR); Florence Sonneville, Paris (FR)

(73) Assignees: INSERM (INSTITUT NATIONAL DE LA SANTE ET DE LA RECHERCHE MEDICALE), Paris (FR); SORBONNE UNIVERSITÉ, Paris (FR)

( * ) Notice: Subject to any disclaimer, the term of this patent is extended or adjusted under 35 U.S.C. 154(b) by 676 days.

(21) Appl. No.: 15/739,366

(22) PCT Filed: Jul. 1, 2016

(86) PCT No.: PCT/EP2016/065565
§ 371 (c)(1),
(2) Date: Dec. 22, 2017

(87) PCT Pub. No.: WO2017/005646
PCT Pub. Date: Jan. 12, 2017

(65) Prior Publication Data
US 2020/0040332 A1 Feb. 6, 2020

(30) Foreign Application Priority Data
Jul. 3, 2015 (WO) .................. PCT/IB2015/001253

(51) Int. Cl.
*C12N 15/113* (2010.01)
*A61P 11/00* (2006.01)

(52) U.S. Cl.
CPC ............ *C12N 15/113* (2013.01); *A61P 11/00* (2018.01); *C12N 15/1138* (2013.01); *C12N 2310/113* (2013.01); *C12N 2310/3231* (2013.01)

(58) Field of Classification Search
CPC ... C12N 15/113; C12N 2310/113; A61P 11/00
See application file for complete search history.

(56) References Cited

PUBLICATIONS

Veit et al (Mol. Biol. Cell 23: 4188-4202, 2012) (Year: 2012).*
Moss (J. Pediatrics 162(4): 676-680, 2013) (Year: 2013).*
Sondo et al (International Journal of Biochemistry & Cell Biology 52: 73-76, 2014) (Year: 2014).*
Huang et al (Proc Natl Acad Sci USA 109:16354-9, 2012) (Year: 2012).*
Huang et al (Proc Natl Acad Sci USA 106:21413-8, 2009) (Year: 2009).*
Caputo et al (Science 322:590-594, 2008) (Year: 2008).*
Caputo et al (Science 322:590-594, 2008, Supplementary Online Material) (Year: 2008).*
GenBank NM_018043.6 retrieved from https://www.ncbi.nlm.nih.gov/nucleotide/NM_018043.6?report=genbank&log$=nuclalign&blast_rank=8&RID=F07FKS2Y016 on Jun. 21, 2020 (Year: 2020).*
Simões et al ("TMEM16A chloride channel does not drive mucus production", Life Science Alliance Nov. 2019, 2 (6) e201900462; DOI: 10.26508/lsa.201900462) (Year: 2019).*
Danahay et al ("Potentiating TMEM16A does not stimulate airway mucus secretion or bronchial and pulmonary arterial smooth muscle contraction", FASEB BioAdvances. 2020;2:464-477) (Year: 2020).*
Ruffin Manon et al: "Anoctamin 1 dysregulation alters bronchial epithelial repair in cystic fibrosis", Biochimica Et Biophysica ACTA. Molecular Basis of Disease, vol. 1832, No. 12, pp. 2340-2351, Sep. 27, 2013.
F. Sonneville et al: "WS06.4 miR-9 and ANO1: Therapeutic targets in cystic fibrosis?", Journal of Cystic Fibrosis, vol. 14, p. S11, Jun. 1, 2015.
Florence Sonneville et al: "New Insights about miRNAs in Cystic Fibrosis", American Journal of Pathology., vol. 185, No. 4, pp. 897-908, Apr. 1, 2015.

* cited by examiner

Primary Examiner — Richard A Schnizer
(74) Attorney, Agent, or Firm — W&C IP

(57) ABSTRACT

The present invention relates to methods and pharmaceutical compositions for the treatment of cystic fibrosis. In particular, the present invention relates to a method of treating cystic fibrosis in a subject in need thereof comprising administering to the subject a therapeutically effective amount of a nucleic acid miR-9 inhibitor.

9 Claims, 12 Drawing Sheets
Specification includes a Sequence Listing.

a/ b/ a/
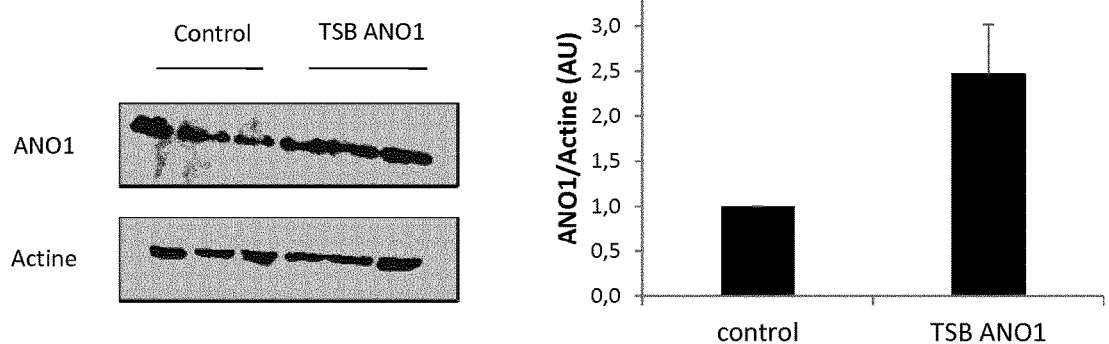
b/
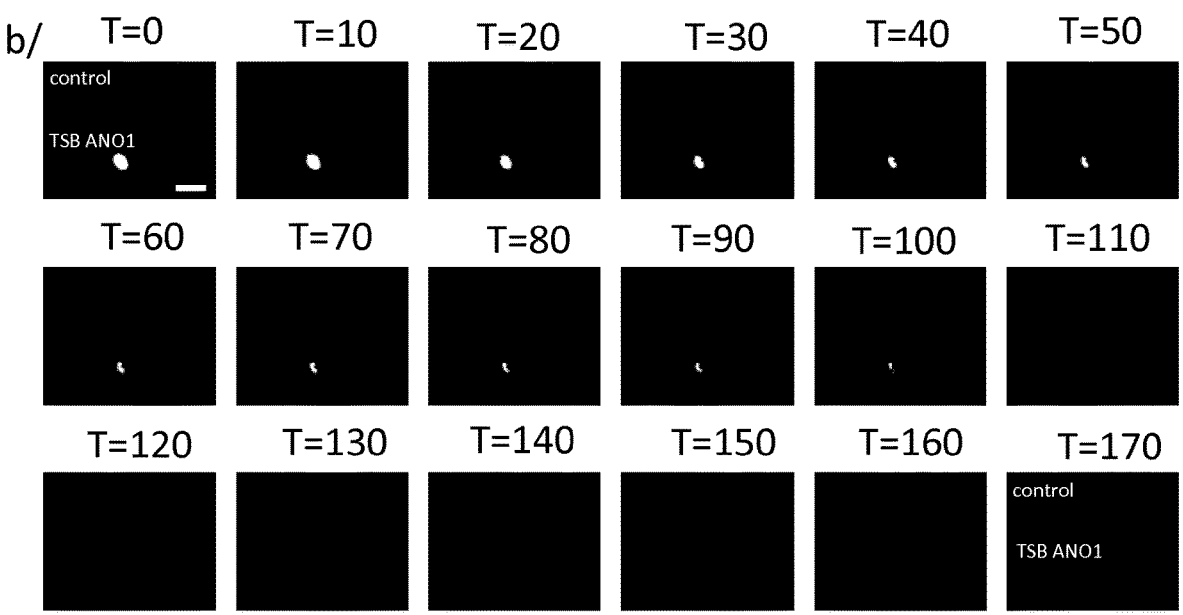
Figures 4a&b

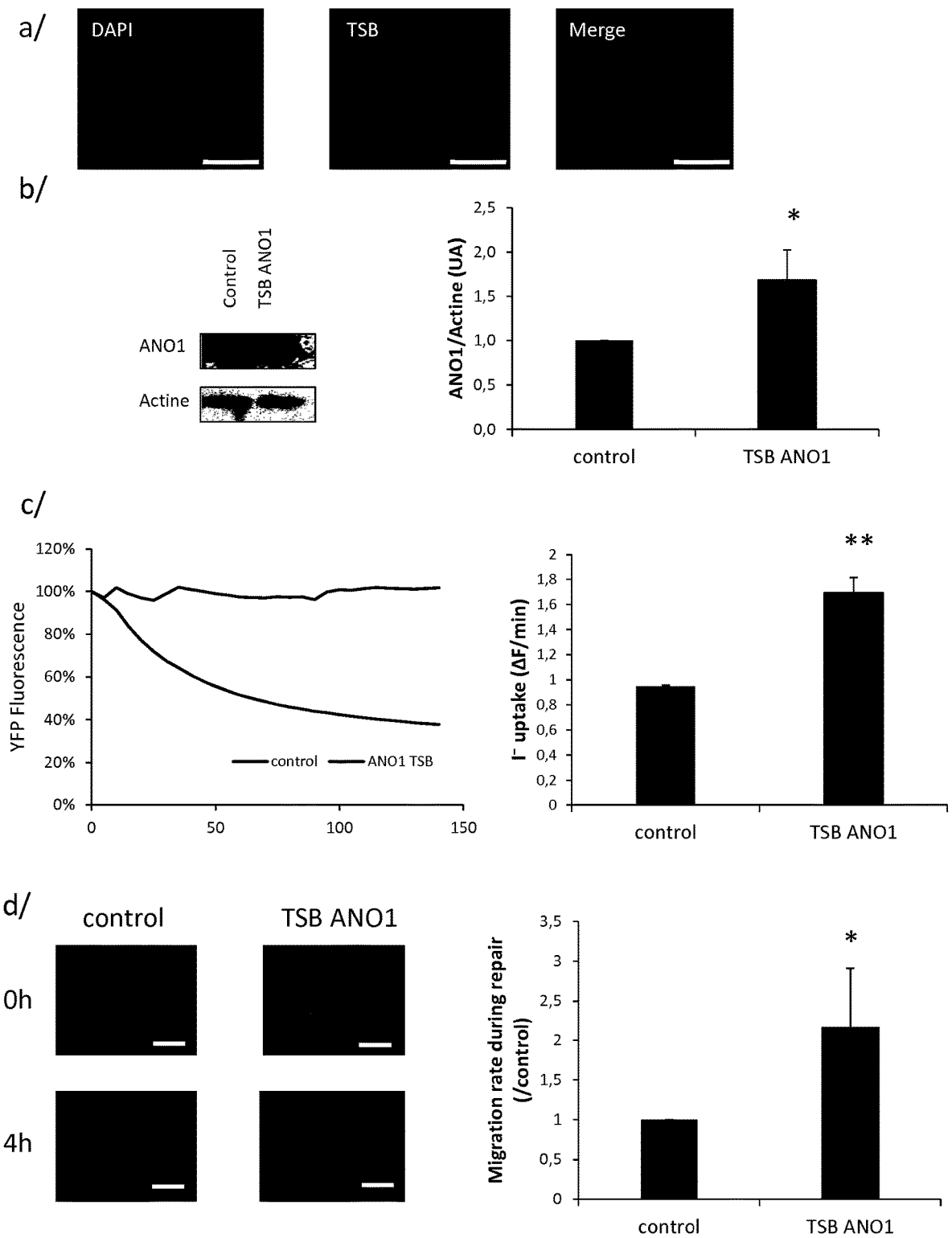
Figures 5a-d

Figure 6D:
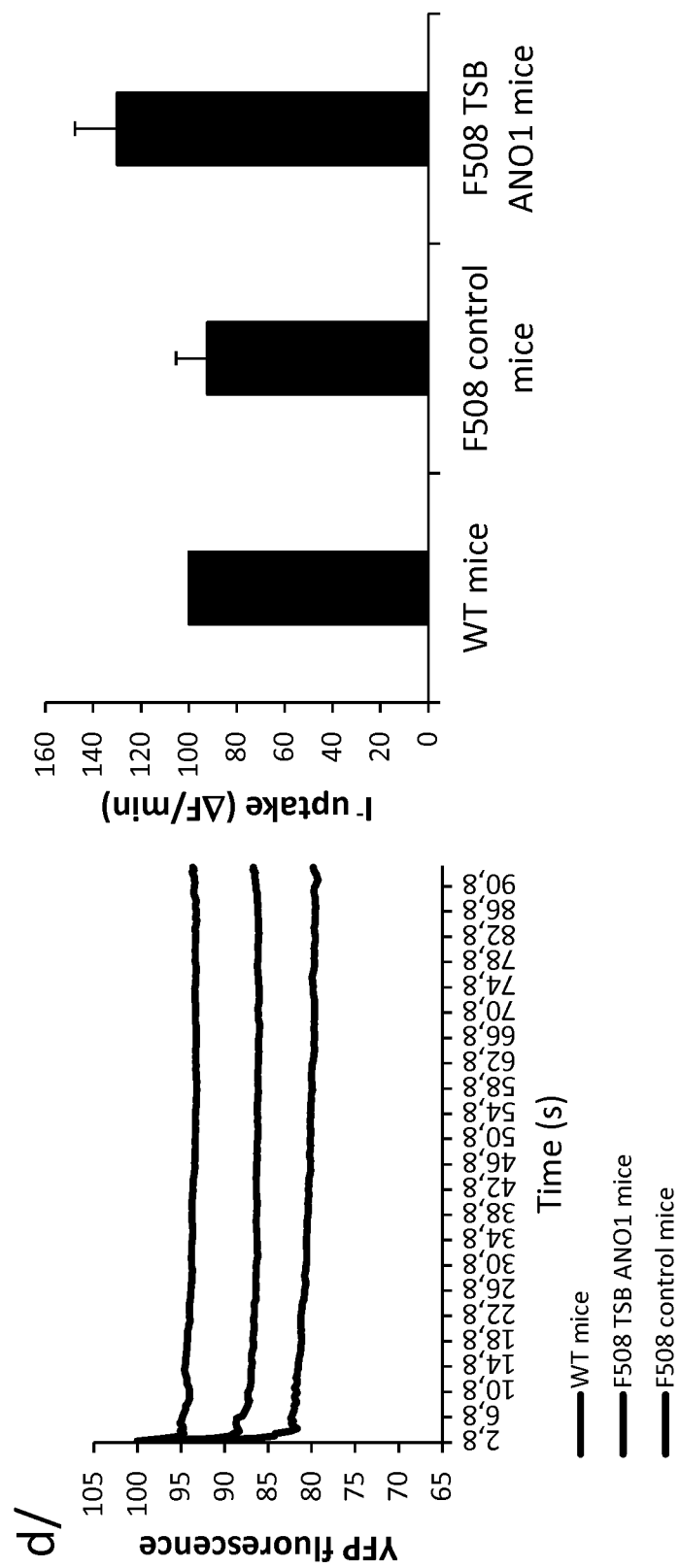

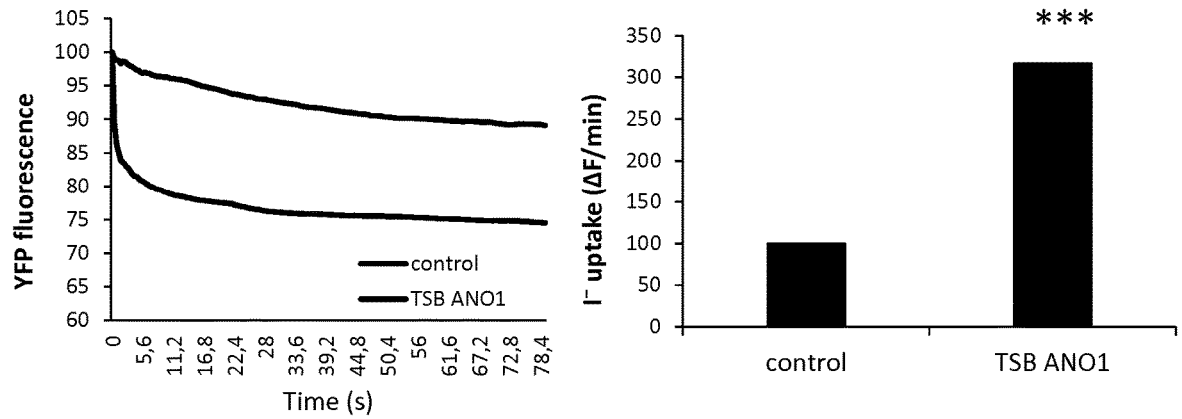
Figure 6a
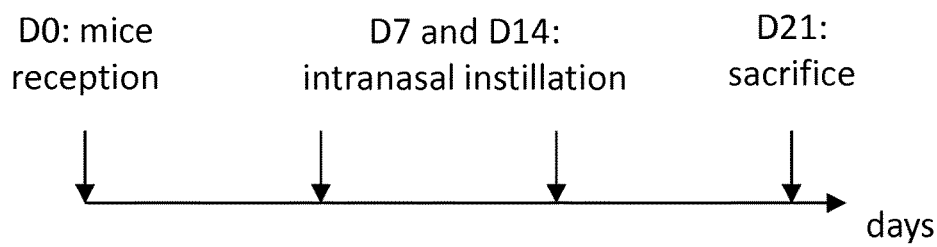
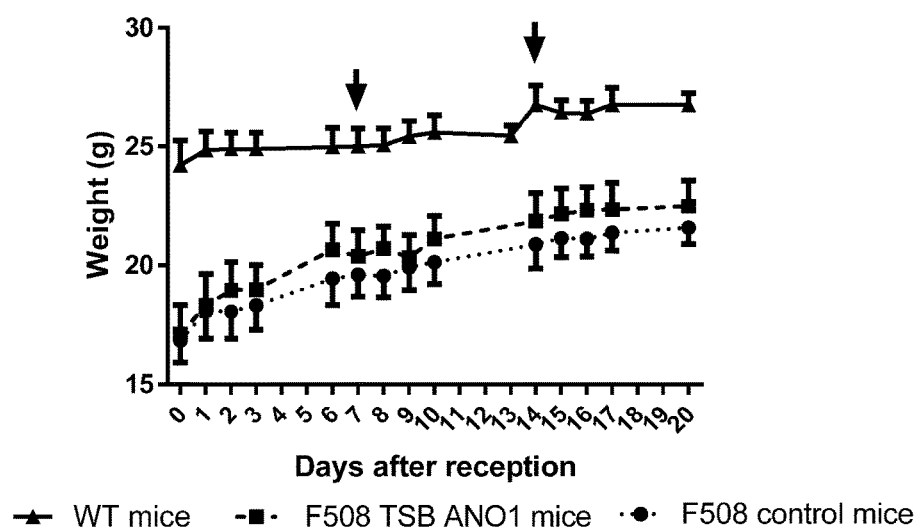
Figures 6b-c

SEQUENCE LISTING

<160> NUMBER OF SEQ ID NOS: 3

<210> SEQ ID NO 1
<211> LENGTH: 4811
<212> TYPE: DNA
<213> ORGANISM: Homo sapiens

<400> SEQUENCE: 1

```
aaaggcgggc cggctggcgt ccaagttcct gaccaggcgc gggccggccc gcgggaccag      60
cagccgggtg gcggcgcgat cggccccgag aggctcaggc gcccccgca tcgagcgcgc     120 gggccggggcg ggccagggcg gcgggcggag cgggaggcgg ccacgtcccc ggcgggcctg     180
ggcgcgggga ggcccggccc cctgcgagcg cgccgcgaac gctgcggtct ccgcccgcag     240
aggccgccgg ggccgtggat ggggagggcg cgccgcccgg cggtcccagc gcacaggcgg     300
ccacgatgag ggtcaacgag aagtactcga cgctcccggc cgaggaccgc agcgtccaca     360
tcatcaacat ctgcgccatc gaggacatcg gctacctgcc gtccgagggc acgctgctga     420
actccttatc tgtggaccct gatgccgagt gcaagtatgg cctgtacttc agggacggcc     480
ggcgcaaggt ggactacatc ctggtgtacc atcacaagag gccctcgggc aaccggaccc     540
tggtcaggag ggtgcagcac agcgacaccc cctctggggc tcgcagcgtc aagcaggacc     600
accccctgcc gggcaagggg gcgtcgctgg atgcaggctc gggggagccc ccgatggact     660
accacgagga tgacaagcgc ttccgcaggg aggagtacga gggcaacctc ctggaggcgg     720
gcctggagct ggagcgggac gaggacacta aaatccacgg agtcgggttt gtgaaaatcc     780
atgccccctg gaacgtgctg tgcagagagg ccgagttttct gaaactgaag atgccgacga     840
agaagatgta ccacattaat gagacccgtg gcctcctgaa aaaaatcaac tctgtgctcc     900
agaaaatcac agatcccatc cagcccaaag tggctgagca caggccccag accatgaaga     960
gactctccta tcccttctcc cgggagaagc agcatctatt tgacttgtct gataaggatt    1020
cctttttcga cagcaaaacc cggagcacga ttgtctatga gatcttgaag agaacgacgt    1080
gtacaaaggc caagtacagc atgggcatca cgagcctgct ggccaatggt gtgtacgcgg    1140
ctgcataccc actgcacgat ggagactaca acggtgaaaa cgtcgagttc aacgacagaa    1200
aactcctgta cgaagagtgg gcacgctatg gagttttcta taagtaccag cccatcgacc    1260
tggtcaggaa gtattttggg gagaagatcg gcctgtactt cgcctggctg ggcgtgtaca    1320
cccagatgct catccctgcc tccatcgtgg gaatcattgt cttcctgtac ggatgcgcca    1380
ccatggatga aacatcccc agcatggaga tgtgtgacca gagacacaat atcaccatgt    1440
```

```
gcccgctttg cgacaagacc tgcagctact ggaagatgag ctcagcctgc ccacggccc    1500 gcgccagcca cctcttcgac aaccccgcca cggtcttctt ctctgtcttc atggccctct    1560
gggctgccac cttcatggag cactggaagc ggaaacagat gcgactcaac taccgctggg    1620
acctcacggg cttgaagag gaagaggag ctgtcaagga tcatcctaga gctgaatacg      1680
aagccagagt cttggagaag tctctgaaga aagagtccag aaacaaagag aagcgccggc   1740
atattccaga ggagtcaaca aacaaatgga agcagagggt taagacagcc atggcgggg    1800 tgaaattgac tgacaaagtg aagctgacat ggagagatcg gttcccagcc tacctcacta    1860
acttggtctc catcatcttc atgattgcag tgacgtttgc catcgtcctc ggcgtcatca    1920
tctacagaat ctccatggcc gccgccttgg ccatgaactc ctcccctcc gtgcggtcca     1980 acatccgggt cacagtcaca gccaccgcag tcatcatcaa cctagtggtc atcatcctcc    2040
tggacgaggt gtatggctgc atagcccgat ggctcaccaa gatcgaggtc ccaaagacgg   2100
agaaaagctt tgaggagagg ctgatcttca aggctttcct gctgaagttt gtgaattcct    2160
acacccccat ctttacgtg gcgttcttca aaggccggtt tgttggacgc ccgggcgact    2220
acgtgtacat tttccgttcc ttccgaatgg aagagtgtgc ccaggggggc tgcctgatgg   2280
agctatgcat ccagctcagc atcatcatgc tggggaaaca gctgatccag aacaacctgt   2340
tcgagatcgg catcccgaag atgaagaagc tcatccgcta cctgaagctg aagcagcaga   2400 gccccctga ccacgaggag tgtgtgaaga ggaaacagcg gtacgaggtg gattacaacc    2460 tggagcccctt cgcgggcctc accccagagt acatggaaat gatcatccag tttggcttcg   2520
tcaccctgtt tgtcgcctcc ttcccctgg ccccactgtt tgcgctgctg aacaacatca    2580
tcgagatccg cctggacgcc aaaaagtttg tcactgagct ccgaaggccg gtagctgtca    2640
gagccaaaga catcggaatc tggtacaata tcctcagagg cattgggaag cttgctgtca    2700
tcatcaatgc cttcgtgatc tccttcacgt ctgacttcat cccgcgcctg gtgtacctct    2760
acatgtacag taagaacggg accatgcacg gcttcgtcaa ccacaccctc tcctccttca    2820
acgtcagtga cttccagaac ggcacggccc ccaatgaccc cctggacctg gctacgagg    2880 tgcagatctg caggtataaa gactaccgag agccgccgtg gtcggaaaac aagtacgaca    2940
tctccaagga cttctgggcc gtcctggcag cccggctggc gtttgtcatc gtcttccaga    3000
acctggtcat gttcatgagc gacttttgtgg actgggtcat cccggacatc cccaaggaca   3060
tcagccagca gatccacaag gagaaggtgc tcatggtgga gctgttcatg cgggaggagc    3120
aagacaagca gcagctgctg gaaacctgga tggagaagga gcggcagaag gacgagccgc    3180
cgtgcaacca ccacaacacc aaagcctgcc cagacagcct cggcagccca gcccccagcc    3240
atgcctacca cgggggcgtc ctgtagctat gccagcgggg ctgggcaggc cagccgggca    3300
tcctgaccga tgggcaccct ctcccagggc aggcggcttc ccgctcccac cagggcccgg    3360
tgggtcctgg gttttctgca aacatggagg accactttct gataggacat tttcctttct    3420
tctttctgtt ttctttccct tgtttttgca caaagccatt atgcagggaa tatttttaa    3480 tctgtagtat tcaagatgaa tcaaaatgat ggctggtaat acggcaataa ggtagcaaag   3540
gcaggtgctt tgcagaaaga atgcttggaa acttgagtct ccctagaggt gaaaagtgag    3600
cagaggcccg tagaaaccct cctctgaatc ctcctaattc cttaagatag atgcaaaatg    3660
gtaagccgag gcatcgcgca aaagctggtg cgatgcttca gggaaaatgg aaacccacg    3720 caagaataat gattgattcc ggttccaaaa ggtgtcacct acctgtttca gaaaagttag    3780
actttccatc gccttttcct tccatcagtt gagtggctga gagagaagtg cctcatccct    3840
```

```
gagccacaca gggggcgtgg gagcatccca gttatccctg gaaagctaga aggggacaga    3900
ggtgtccctg attaagcagg aaacagcacc cttggcgtcc ccagcaggct ccccactgtc    3960
agccacacac ctgcccccat cacaccaagc cgacctcaga gttgttcatc ttccttatgg    4020
gacaaaaccg gttgaccaga aaatgggcag agagagatga cctcggaagc atttccacag    4080
atggtgtcag ggtttcaaga agtcttaggg cttccagggg tcccctggaa gctttagaat    4140
atttatgggt ttttttttca aatatcaatt atatggtaga ttgaggattt tttttctgta    4200
gctcaaaggt ggagggagtt tattagttaa ccaaatatcg ttgagaggaa tttaaaatac    4260
tgttactacc aaagattttt attaataaag gcttatattt tggtaacact tctctatatt    4320
tttactcaca ggaatgtcac tgttggacaa ttattttaaa agtgtataaa accaagtctc    4380
ataaatgata tgagtgatct aaatttgcag caatgatact aaacaactct ctgaaatttc    4440
tcaagcacca agagaaacat cattttagca aaggccagga ggaaaaatag aaataaattt    4500
gtcttgaaga tctcattgat gtgatgttac attcccttta atctgccaac tgtggtcaaa    4560
gttcataggt gtcgtacatt tccattattt gctaaaatca tgcaatctga tgcttctctt    4620
ttctcttgta cagtaagtag tttgaagtgg gttttgtata taaatactgt attaaaaatt    4680
aggcaattac caaaaatcct tttatggaaa ccatttttt aaaaagtgaa tgtacacaaa     4740
tccacagagg actgtggctg gacattcatc taaataaatt tgaatatacg acacttttct    4800
cacttgaaaa a                                                        4811

<210> SEQ ID NO 2
<211> LENGTH: 23
<212> TYPE: RNA
<213> ORGANISM: Homo sapiens

<400> SEQUENCE: 2
ucuuugguua ucuagcugua uga                                              23

<210> SEQ ID NO 3
<211> LENGTH: 21
<212> TYPE: DNA
<213> ORGANISM: Artificial Sequence
<220> FEATURE:
<223> OTHER INFORMATION: Synthetic TBS

<400> SEQUENCE: 3
ttttctccgt ctttgggacc t                                                21
```

METHODS AND PHARMACEUTICAL COMPOSITIONS FOR THE TREATMENT OF CYSTIC FIBROSIS

FIELD OF THE INVENTION

The present invention relates to methods and pharmaceutical compositions for the treatment of cystic fibrosis.

BACKGROUND OF THE INVENTION

Cystic fibrosis (CF) is a genetic disease caused by mutations in the gene encoding the CFTR Cl− channel (Riordan, 1989). CF affects several organs, but the most severe consequences are observed in the lung. The pathogenesis of lung disease in CF is still not perfectly understood. The loss of CFTR channel function in CF favors the colonization of the airway surface by highly virulent bacteria. However, the mechanism by which this happens is still a matter of debate. CFTR channel activity is certainly an important contributor to mucociliary clearance. The fine balance between CFTR-dependent Cl− secretion and Na+ absorption through the ENaC channel controls the thickness of the periciliary fluid (PCF). In the absence of functional CFTR, fluid absorption prevails over secretion. This imbalance dehydrates the airway surface thereby impairing ciliary beating. Immobilized mucus then becomes a niche for bacterial survival and proliferation. Activation of an alternative chloride channel may be an attractive therapeutic strategy in cystic fibrosis. This approach could be applied to all patients irrespective of their genotype. Instead, therapies aimed at CFTR need to be mutation-specific, an approach that may not be applicable to all classes of mutations. The activation of an alternative chloride channel in CF airways could be beneficial by providing a route for chloride and bicarbonate secretion needed to ameliorate mucociliary clearance and restore anti-microbial activity. More than 20 years ago, it was found that airway epithelial cells possess a second type of Cl− secretory pathway. While CFTR is regulated by cAMP, the second pathway is activated by the increase in cytosolic Ca2+ concentration. Stimulation of airway epithelia with purinergic agonists such as ATP or UTP causes a strong, but transient, burst of transepithelial Cl− transport. This effect is dependent on both releases of Ca2+ from intracellular stores and influx of Ca2+ through the plasma membrane. Ca2+-activated Cl− secretion is independent of CFTR since it is not defective in CF patients. Interestingly, stimulation of Ca2+-dependent Cl− secretion has a positive effect on PCF thickness. This effect suggests that stimulation of the Ca2+-dependent pathway may compensate for defective CFTR. The orphan protein TMEM16A was identified as a component of Ca2+-activated chloride channel (CaCC). TMEM16A, also known as anoctamin-1 (ANO1), belongs to a protein family composed of 10 members whose primary sequence and predicted structure (eight transmembrane domains) have no similarity with those of other anion channels. However, previous works have shown that TMEM16A activity and expression were reduced in a CF context by an unknown mechanism.

SUMMARY OF THE INVENTION

The present invention relates to methods and pharmaceutical compositions for the treatment of cystic fibrosis. In particular, the present invention is defined by the claims.

DETAILED DESCRIPTION OF THE INVENTION

The aim of the inventors was to understand the origin of the reduced expression of ANO1 in CF by studying the role of miRNAs which regulate negatively gene expression. Thus, the inventors performed bio-informatic approaches to study miRNAs that could target ANO1 and evaluated the expression levels of miRNAs candidates by RT-qPCR in bronchial epithelial cells lines. They performed functionality experiments studying the miRNAs candidates binding to the 3'UTR of ANO1 over-expressing miRNAs, and quantifying the expression of ANO1 in these conditions. They also evaluated cells migration rate and ANO1 chloride activity modulating a miRNA which regulates ANO1. The inventors have identified different miRNAs including miR-9 as a potential regulator of ANO1. They observed that miR-9 is overexpressed in CF cells and a decrease of ANO1 expression and luciferase activity when they overexpress miR-9 in CF and non-CF cells. Furthermore, the inventors observed a decrease of cells migration rate and ANO1 chloride activity when miR-9 is overexpressed. In conclusion, the results showed that miR-9 directly regulates ANO1 by pairing to its 3'UTR, and that modulate miR-9 allows to change cells migration rate and ANO1 chloride activity.

Accordingly a first object of the present invention relates to a method of treating cystic fibrosis in a subject in need thereof comprising administering to the subject a therapeutically effective amount of a nucleic acid miR-9 inhibitor.

As used herein, the term "subject" denotes a mammal. A subject according to the invention refers to any subject (preferably human) afflicted or at risk to be afflicted with cystic fibrosis. The method of the invention may be performed for any type of cystic fibrosis such as revised in the World Health Organisation Classification of cystic fibrosis and selected from the E84 group: mucoviscidosis, Cystic fibrosis with pulmonary manifestations, Cystic fibrosis with intestinal manifestations and Cystic fibrosis with other manifestations.

As used herein, the term "ANO1" has its general meaning in the art and refers to the anoctamin-1 protein, also known as TMEM16A. ANO1 belongs to a protein family composed of 10 members whose primary sequence and predicted structure (eight transmembrane domains) have no similarity with those of other anion channels. An exemplary human nucleic acid sequence is the NCBI Reference Sequence NM_018043.5 (SEQ ID NO:1).

SEQ ID NO: 1

```
  1 aaaggcgggc cggctggcgt ccaagttcct gaccaggcgc gggccggccc gcgggaccag 61 cagccgggtg gcggcgcgat cggccccgag aggctcaggc gccccccgca tcgagcgcgc 121 gggccgggcg ggccagggcg gcgggcggag cgggaggcgg ccacgtcccc ggcgggcctg 181 ggcgcgggga ggcccggccc cctgcgagcg cgccgcgaac gctgcggtct ccgcccgcag 241 aggccgccgg ggccgtggat ggggagggcg cgccgcccgg cggtcccagc gcacaggcgg
```

-continued

```
 301 ccacgatgag ggtcaacgag aagtactcga cgctcccggc cgaggaccgc agcgtccaca
 361 tcatcaacat ctgcgccatc gaggacatcg gctacctgcc gtccgagggc acgctgctga
 421 actccttatc tgtggaccct gatgccgagt gcaagtatgg cctgtacttc agggacggcc
 481 ggcgcaaggt ggactacatc ctggtgtacc atcacaagag gccctcgggc aaccggaccc
 541 tggtcaggag ggtgcagcac agcgacaccc cctctggggc tcgcagcgtc aagcaggacc
 601 acccctgcc gggcaagggg gcgtcgctgg atgcaggctc gggggagccc ccgatggact
 661 accacgagga tgacaagcgc ttccgcaggg aggagtacga gggcaacctc ctggaggcgg
 721 gcctggagct ggagcgggac gaggacacta aaatccacgg agtcgggttt gtgaaaatcc
 781 atgcccctg aacgtgctg tgcagagagg ccgagtttct gaaactgaag atgccgacga
 841 agaagatgta ccacattaat gagacccgtg gcctcctgaa aaaaatcaac tctgtgctcc
 901 agaaaatcac agatcccatc cagcccaaag tggctgagca caggccccag accatgaaga
 961 gactctccta tcccttctcc cgggagaagc agcatctatt tgacttgtct gataaggatt
1021 cctttttcga cagcaaaacc cggagcacga ttgtctatga tcttgaag agaacgacgt
1081 gtacaaaggc caagtacagc atgggcatca cgagcctgct ggccaatggt gtgtacgcgg
1141 ctgcataccc actgcacgat ggagactaca acggtgaaaa cgtcgagttc aacgacagaa
1201 aactcctgta cgaagagtgg gcacgctatg gagttttcta taagtaccag cccatcgacc
1261 tggtcaggaa gtatttgggg gagaagatcg gcctgtactt cgcctggctg ggcgtgtaca
1321 cccagatgct catccctgcc tccatcgtgg aatcattgt cttcctgtac ggatgcgcca
1381 ccatggatga aacatcccc agcatggaga tgtgtgacca gagacacaat atcaccatgt
1441 gcccgctttg cgacaagacc tgcagctact ggaagatgag ctcagcctgc gccacggccc
1501 gcgccagcca cctcttcgac aaccccgcca cggtcttctt ctctgtcttc atggccctct
1561 gggctgccac cttcatggag cactggaagc ggaaacagat gcgactcaac taccgctggg
1621 acctcacggg ctttgaagag gaagaggagg ctgtcaagga tcatcctaga gctgaatacg
1681 aagccgagt cttggagaag tctctgaaga aagagtccag aaacaaagag aagcgccggc
1741 atattccaga ggagtcaaca aacaaatgga agcagagggt taagacagcc atggcggggg
1801 tgaaattgac tgacaaagtg aagctgacat ggagagatcg gttcccagcc tacctcacta
1861 acttggtctc catcatcttc atgattgcag tgacgtttgc catcgtcctc ggcgtcatca
1921 tctacagaat ctccatggcc gccgccttgg ccatgaactc ctccccctcc gtgcggtcca
1981 acatccgggt cacagtcaca gccaccgcag tcatcatcaa cctagtggtc atcatcctcc
2041 tggacgaggt gtatggctgc atagcccgat ggctcaccaa gatcgaggtc ccaaagacgg
2101 agaaaagctt tgaggagagg ctgatcttca aggctttcct gctgaagttt gtgaattcct
2161 acacccccat cttttacgtg gcgttcttca aaggccggtt tgttggacgc ccgggcgact
2221 acgtgtacat tttccgttcc ttccgaatgg aagagtgtgc gccaggggc tgcctgatgg
2281 agctatgcat ccagctcagc atcatcatgc tggggaaaca gctgatccag aacaacctgt
2341 tcgagatcgg catcccgaag atgaagaagc tcatccgcta cctgaagctg aagcagcaga
2401 gccccctga ccacgaggag tgtgtgaaga ggaaacagcg gtacgaggtg gattacaacc
2461 tggagccctt cgcgggcctc accccagagt acatggaaat gatcatccag tttggcttcg
2521 tcaccctgtt tgtcgcctcc ttccccctgg ccccactgtt tgcgctgctg aacaacatca
2581 tcgagatccg cctggacgcc aaaaagtttg tcactgagct ccgaaggccg gtagctgtca
2641 gagccaaaga catcggaatc tggtacaata tcctcagagg cattgggaag cttgctgtca
```

```
-continued
2701 tcatcaatgc cttcgtgatc tccttcacgt ctgacttcat cccgcgcctg gtgtacctct 2761 acatgtacag taagaacggg accatgcacg gcttcgtcaa ccacaccctc tcctccttca 2821 acgtcagtga cttccagaac ggcacggccc ccaatgaccc cctggacctg ggctacgagg 2881 tgcagatctg caggtataaa gactaccgag agccgccgtg gtcggaaaac aagtacgaca 2941 tctccaagga cttctgggcc gtcctggcag cccggctggc gtttgtcatc gtcttccaga 3001 acctggtcat gttcatgagc gactttgtgg actgggtcat cccggacatc cccaaggaca 3061 tcagccagca gatccacaag gagaaggtgc tcatggtgga gctgttcatg cgggaggagc 3121 aagacaagca gcagctgctg gaaacctgga tggagaagga gcggcagaag gacgagccgc 3181 cgtgcaacca ccacaacacc aaagcctgcc cagacagcct cggcagccca gccccagcc 3241 atgcctacca cggggcgtc ctgtagctat gccagcgggg ctgggcaggc cagccgggca 3301 tcctgaccga tgggcaccct ctcccagggc aggcggcttc ccgctccac cagggcccgg 3361 tgggtcctgg gttttctgca acatggagg accactttct gataggacat tttcctttct 3421 tctttctgtt ttctttccct tgttttttgca caaagccatt atgcagggaa tattttttaa 3481 tctgtagtat tcaagatgaa tcaaaatgat ggctggtaat acggcaataa ggtagcaaag 3541 gcaggtgctt tgcagaaaga atgcttggaa acttgagtct ccctagaggt gaaaagtgag 3601 cagaggcccg tagaaaccct cctctgaatc ctcctaattc cttaagatag atgcaaaatg 3661 gtaagccgag gcatcgcgca aaagctggtg cgatgcttca gggaaaatgg aaaacccacg 3721 caagaataat gattgattcc ggttccaaaa ggtgtcacct acctgtttca gaaaagttag 3781 actttccatc gccttttcct tccatcagtt gagtggctga gagagaagtg cctcatccct 3841 gagccacaca gggggcgtgg gagcatccca gttatccctg gaaagctaga aggggacaga 3901 ggtgtccctg attaagcagg aaacagcacc cttggcgtcc ccagcaggct ccccactgtc 3961 agccacacac ctgcccccat cacaccaagc cgacctcaga gttgttcatc ttccttatgg 4021 gacaaaaccg gttgaccaga aaatgggcag agagagatga cctcggaagc atttccacag 4081 atggtgtcag ggtttcaaga agtcttaggg cttccagggg tcccctggaa gctttagaat 4141 atttatgggt ttttttttca aatatcaatt atatggtaga ttgaggattt ttttctgta 4201 gctcaaaggt ggagggagtt tattagttaa ccaaatatcg ttgagaggaa tttaaaatac 4261 tgttactacc aaagattttt attaataaag gcttatattt tggtaacact tctctatatt 4321 tttactcaca ggaatgtcac tgttggacaa ttattttaaa agtgtataaa accaagtctc 4381 ataaatgata tgagtgatct aaatttgcag caatgatact aaacaactct ctgaaattttc 4441 tcaagcacca agagaaacat cattttagca aaggccagga ggaaaaatag aaataaattt 4501 gtcttgaaga tctcattgat gtgatgttac attcccttta atctgccaac tgtggtcaaa 4561 gttcataggt gtcgtacatt tccattattt gctaaaatca tgcaatctga tgcttctctt 4621 ttctcttgta cagtaagtag tttgaagtgg gttttgtata taaatactgt attaaaaatt 4681 aggcaattac caaaaatcct tttatggaaa ccatttttt aaaaagtgaa tgtacacaaa 4741 tccacagagg actgtggctg gacattcatc taaataaatt tgaatatacg acactttcct 4801 cacttgaaaa a
```

The term "miRNAs" refers to mature microRNA (non-coding small RNAs) molecules that are generally 21 to 22 nucleotides in length, even though lengths of 19 and up to 23 nucleotides have been reported. miRNAs are each processed from longer precursor RNA molecules ("precursor miRNA": pri-miRNA and pre-miRNA). Pri-miRNAs are transcribed either from non-protein-encoding genes or embedded into protein-coding genes (within introns or non-coding exons). The "precursor miRNAs" fold into hairpin structures containing imperfectly base-paired stems and are processed in two steps, catalyzed in animals by two Ribonuclease III-type endonucleases called Drosha and Dicer. The processed miRNAs (also referred to as "mature miRNA") are assembled into large ribonucleoprotein complexes (RISCs) that can associate them with their target mRNA in order to repress translation. All the miRNAs pertaining to the invention are known per se and sequences of them are publicly available from the data base mirbase.org/cgi-bin/mirna_summary.pl?org=hsa. As used herein, the "miR-9" microRNA (homologous to miR-79), is a short non-coding RNA gene involved in gene regulation. The mature ~21nt miRNAs are processed from hairpin precursor sequences by the Dicer enzyme. The dominant mature miRNA sequence is processed from the 5' arm of the miR-9 precursor, and from the 3' arm of the mir-79 precursor. The mature products are thought to have regulatory roles through complementarity to mRNA. An exemplary sequence of miR-9 is found on MiRBase reference sequence MIMAT0000441 (UCUUUGGUUAUCUAGCUGUAUGA=SEQ ID NO:2).

As described herein, a "nucleic acid miR-9 inhibitor" (i.e. a nucleic acid that inhibits miR-9) is any nucleic acid, for example, an oligonucleotide, that reduces (i.e. inhibits) the biological activity of miR-9. In some embodiments, nucleic acid miR-9 inhibitors comprise a nucleic acid sequence that is complementary to at least a portion of the nucleic acid sequence of either miR-9 itself or the target mRNA sequences of miR-9; inhibition of miR-9 therefore occurs by binding of the inhibitor to miR-9 or to its target mRNA. In both cases, miR-9 is prevented from recognizing and binding its target sequence and thus cannot induce gene silencing. The nucleic acid miR-9 inhibitor of the invention may comprise a structure that is single stranded, double stranded, partially double-stranded, or hairpin in nature.

In some embodiments, the nucleic acid miR-9 inhibitor binds to miR-9. Thus, in some embodiments, the nucleic acid miR-9 inhibitor binds to and sequesters miR-9, so preventing it from binding to its target mRNA sequences. Binding occurs via complementary base pairing between at least one nucleotide present in the nucleic acid miR-9 inhibitor and a corresponding nucleotide present in miR-9, such that at least a portion of the nucleic acid miR-9 inhibitor and miR-9 together define a base-paired nucleic acid duplex. Said complementary base pairing (and thus duplex formation) can occur over a region of two or more contiguous nucleotides of miR-9 (e.g. 3, 4, 5, 6, 7, 8, 9, 10, 11, 12, 13, 14, 15, 16, 17, 18, 19, 20 or 21 contiguous nucleotides). A base-paired nucleic acid duplex formed when the nucleic acid miR-9 inhibitor binds to miR-9 (as described above) may comprise one or more mismatch pairings. In some embodiments, two or more regions of complementary base-paired nucleic acid duplex (e.g. 3, 4, 5 or 6) are formed, wherein each region is separated from the next by one or more mismatch pairings. As used herein, the term "complementary" refers to a nucleic acid molecule that forms hydrogen bonds with another nucleic acid molecule with Watson-Crick base pairing. Watson-Crick base pairing refers to the following hydrogen bonded nucleotide pairings: A:T and C:G (for DNA); and A:U and C:G (for RNA). For example, two or more complementary nucleic acid molecule strands can have the same number of nucleotides (i.e. have the same length and form one double-stranded region, with or without an overhang) or have a different number of nucleotides (e.g. one strand may be shorter than but fully contained within another strand or one strand may overhang the other strand). Mismatch pairings are formed between any two nucleotide bases that together do not form one of the hydrogen-bonded standard Watson-Crick base pairs of A:U (in RNA), A:T (in DNA) and C:G (in both RNA and DNA). In some embodiments, the nucleic acid miR-9 inhibitor comprises a nucleic acid sequence complementary to at least a portion of the miR-9 sequence. The nucleic acid miR-9 inhibitor may comprise a nucleic acid sequence complementary to 2, 3, 4, 5, 6, 7, 8, 9, 10, 11, 12, 13, 14, 15, 16, 17, 18, 19, 20 or 21 contiguous nucleotides of miR-9.

In some embodiments, the nucleic acid miR-9 inhibitor comprises a nucleic acid sequence having at least 70% sequence identity to a complementary (i.e. antisense) sequence of miR-9. According to the invention a first nucleic acid sequence having at least 70% of identity with a second nucleic acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99 or 100% of identity with the second nucleic acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997. Thus, in some embodiments, the nucleic acid miR-9 inhibitor comprises a sequence complementary to miR-9. In some embodiments, the nucleic acid miR-9 inhibitor comprises a nucleic acid sequence that differs from the complementary (i.e. antisense) sequence of miR9 at a maximum of 10 (e.g. a maximum of 10, 9, 8, 7, 6, 5, 4, 3, 2, or 1) nucleotide positions. In some embodiments, the nucleic acid miR-9 inhibitor comprises a nucleic acid sequence that differs from the complementary (i.e. antisense) sequence of miR9 at a maximum of 5 (e.g. a maximum of 4, 3, 2, or 1) nucleotide positions. Thus, said nucleic acid sequence is identical to the complementary (i.e. antisense) sequence of miR9 except at a limited number of nucleotide positions. In some embodiments, the nucleic acid miR-9 inhibitor, as described above, has a maximum length of 60 (for example 55, 50, 45, 40, 35, 30, or 25) nucleotides.

In some embodiments, the nucleic acid miR-9 inhibitor is a miR-9 antagomir. As used herein, an "antagomir" is a nucleic acid oligomer that is designed to bind to a specific target microRNA via complementary base pairing (for example, as described above). An antagomir may have a sequence that is wholly or partially complementary to the microRNA target sequence. Antagomirs may have a single stranded, double stranded, partially double-stranded, or hairpin structure. Antagomirs may further comprise chemically modified nucleotides (e.g. as described below). Methods for designing and creating antagomirs are known in the art.

In some embodiments, the nucleic acid miR-9 inhibitor is a miR-9 microRNA-sponge. As used herein, the term "microRNA-sponge" is a nucleic acid that comprises multiple (e.g. at least 2, 3, 4, 5 or 6) binding sites for a specific target microRNA. Thus, a microRNA-sponge is able to bind and sequester multiple target microRNA molecules. A microRNA sponge may comprise an mRNA expressed from a vector (e.g. a viral vector or plasmid vector). The presence in a microRNA-sponge of multiple binding sites for the target microRNA enables microRNAs to be adsorbed in a manner analogous to a sponge soaking up water. A microRNA-sponge may bind target microRNAs via complementary base pairing (for example, as described above). Thus, a microRNA-sponge may comprise multiple (e.g. at least 2, 3, 4, 5 or 6) nucleic acid sequences, each sequence being complementary to at least a portion of the microRNA target sequence. A microRNA-sponge may comprise multiple (e.g. at least 2, 3, 4, 5 or 6) nucleic acid sequences, wherein each sequence is complementary to the microRNA target sequence. Methods for designing and creating microRNA-sponges are known in the art. In some embodiments, the nucleic acid miR-9 inhibitor comprising two or more nucleic acid sequences, wherein each of said two or more nucleic acid sequences has at least 70% sequence identity to the complementary (i.e. antisense) sequence of miR9 is a miR-9 microRNA sponge.

Thus, in some embodiments, the nucleic acid miR-9 inhibitor does not bind directly to miR-9 but instead binds to a miR-9 mRNA target site in the ANO1 nucleic acid sequence. This has the effect of blocking said target site (for example, by steric interference), preventing its recognition and binding by miR-9, and thus inhibiting miR-9 and its actions. In contrast to the binding of miR-9 to an mRNA target site, the binding of the nucleic acid miR-9 inhibitor of the invention to a miR-9 mRNA target site does not induce gene silencing (e.g. by mRNA degradation or translational repression) of said target mRNA. In some embodiments, the miR-9 mRNA target site is located on an ANO1 3'UTR. In some embodiments, the miR-9 inhibitor is a Target Site Blocker (TSB). Binding of the nucleic acid miR-9 inhibitor to a miR-9 mRNA target site may occur via complementary base pairing, as described above. Thus, in some embodiments, binding between the nucleic acid miR-9 inhibitor and the miR-9 mRNA target site occurs via complementary base pairing between at least one nucleotide present in the nucleic acid miR-9 inhibitor and a corresponding nucleotide present in the miR-9 mRNA target site, such that at least a portion of the nucleic acid miR-9 inhibitor and the miR-9 mRNA target site together define a base-paired nucleic acid duplex. Said complementary base pairing (and thus duplex formation) can occur over a region of two or more contiguous nucleotides of the miR-9 mRNA target site (e.g. 3, 4, 5, 6, 7, 8, 9, 10, 11, 12, 13, 14, 15, 16, 17, 18, 19, 20 or 21 contiguous nucleotides). A base-paired nucleic acid duplex formed when the nucleic acid miR-9 inhibitor binds to the miR-9 mRNA target (as described above) may comprise one or more mismatch pairings. In some embodiments, two or more regions of complementary base-paired nucleic acid duplex (e.g. 3, 4, 5 or 6) are formed, wherein each region is separated from the next by one or more mismatch pairings. In some embodiments, the mRNA target site is located on the 3'UTR (untranslated region) of the target ANO1 mRNA. In some embodiments, wherein the nucleic acid miR-9 inhibitor competes with miR-9 for binding to a miR-9 mRNA target site, the nucleic acid comprises the nucleic acid sequence TTTTCTCCGTCTTTGGGACCT (SEQ ID NO: 3). Thus, said nucleic acid sequence will bind to the miR-9 mRNA target site in ANO1 via complementary binding at the location targeted by the seed region of miR-9, thus preventing miR-9 from binding.

In some embodiments, the nucleic acid miR-9 inhibitor is a small interfering RNA (siRNA) that is targeted against miR-9. As used herein the term "siRNA" has its general meaning in the art and refers to a double-stranded interfering RNA. siRNA useful in the present methods comprise short double-stranded RNA from about 17 nucleotides to about 29 nucleotides in length, preferably from about 19 to about 25 nucleotides in length. The siRNA comprise a sense RNA strand, and a complementary antisense RNA strand annealed together by standard Watson-Crick base-pairing interactions (hereinafter "base-paired"). The sense strand comprises a nucleic acid sequence which is substantially identical to a nucleic acid sequence contained within the target miRNA. As used herein, a nucleic acid sequence in a siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area. The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides. One or both strands of the siRNA can also comprise a 3 overhang. As used herein, a "3' overhang" refers to at least one unpaired nucleotide extending from the 3'-end of a duplexed RNA strand. Thus, in one embodiment, the siRNA comprises at least one 3' overhang of 1 to about 6 nucleotides (which includes ribonucleotides or deoxyribonucleotides) in length, preferably from 1 to about 5 nucleotides in length, more preferably from 1 to about 4 nucleotides in length, and particularly preferably from about 2 to about 4 nucleotides in length. In a preferred embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The nucleic acid miR-9 inhibitor of the invention may be a ribonucleic acid (RNA) or a deoxyribonucleic acid (DNA), or may comprise both RNA and DNA. Thus, in some embodiments, a nucleic acid miR-9 inhibitor (as described above) comprises RNA. In some embodiments, a nucleic acid miR-9 inhibitor (as described above) comprises DNA. Unless specifically indicated otherwise, nucleic acid sequences in this document are written in the direction 5'-3'. As would be understood by a person skilled in the art, nucleic acid sequences written as RNA and containing the nucleotide U may equally be written as DNA by substituting T for U. Reference to nucleic acid(s) and/or nucleotide(s) embraces modified nucleic acid(s) and modified nucleotide (s). For example, a nucleic acid or nucleotide may be modified to increase the stability of said nucleic acid or nucleotide, for instance by improving resistance to nuclease degradation. In some embodiments, a modified nucleic acid comprises a locked nucleic acid (LNA) nucleotide. In more detail, the ribose moiety of an LNA nucleotide is modified with an extra bridge connecting the 2' oxygen and 4' carbon. The bridge "locks" the ribose in the 3'-endo (North) conformation, which is often found in A-form nucleic acid duplexes. LNA nucleotides can be mixed with DNA or RNA residues in an oligonucleotide whenever desired. The locked ribose conformation enhances base stacking and backbone pre-organization. This significantly increases the hybridization properties (melting temperature) of oligonucleotides. Other examples of modified nucleotides include 2'-methoxy-ethoxy (MOE) nucleotides; 2'-methyl-thio-ethyl, 2'-deoxy-2'-fluoro nucleotides. 2'-deoxy-2'-chloro nucleotides, 2'-azido nucleotides, and 2'-O-methyl nucleotides. A nucleic acid molecule of the invention may also be conjugated to one or more cholesterol moieties. Thus, in some embodiments, the nucleic acid miR-9 inhibitor is conjugated to at least one (for example, 1, 2, 3, or 4) cholesterol moiety. A nucleic acid miR-9 inhibitor of the invention may be constructed such that all of its nucleotides are modified nucleotides. Thus, in some embodiments, the nucleic acid miR-9 inhibitor consists of modified nucleotides. In some embodiments, said modified nucleotides consist of LNA nucleotides, or 2'-O-methyl modified nucleotides, or 2'-0-methoxy-ethyl modified nucleotides, or 2'-fluoro modified nucleotides. In some embodiments, the nucleic acid miR-9 inhibitor is a synthetic 2'-O-methyl RNA oligonucleotide, and which competes with miR-9 target mRNAs with stronger binding to the miRNA-associated gene silencing complex. Nucleic acid analogs are composed of three parts: a phosphate backbone, a pucker-shaped pentose sugar, either ribose or deoxyribose, and one of four nucleobases. An analog may have any of these altered. Typically the analog nucleobases confer, among other things, different base pairing and base stacking proprieties. Examples include universal bases, which can pair with all four canon bases, and phosphate-sugar backbone analogs such as PNA, which affect the properties of the chain. Artificial nucleic acids include peptide nucleic acid (PNA), Morpholino and LNA, as well as glycol nucleic acid (GNA) and threose nucleic acid (TNA). Each of these is distinguished from naturally-occurring DNA or RNA by changes to the backbone of the molecule. Thus, in some embodiments, the nucleic acid miR-9 inhibitor (as described above) is a nucleic acid analog selected from: a peptide nucleic acid (PNA), a glycol nucleic acid (GNA), a threose nucleic acid (TNA), and a morpholino. The nucleic acid miR-9 inhibitor (as described above) may comprise at least one (e.g. 1, 2, 3, 4, 5, 6, 7, 8, 9, 10, 12, 14, 16, 18 or 20) modified phosphodiester linkage. In some embodiments, the modified phosphodiester linkage is a phosphorothioate linkage. In some embodiments, all of the phosphodiester linkages are modified phosphodiester linkages.

The nucleic acid molecules of the invention may be made using any suitable process known in the art. Thus, the nucleic acid molecules may be made using chemical synthesis techniques. Alternatively, the nucleic acid molecules of the invention may be made using molecular biology techniques.

In one aspect, the invention provides a nucleic acid vector comprising a nucleic acid sequence encoding a nucleic acid miR-9 inhibitor as described above. For example, the nucleic acid molecules of the present invention may be delivered into a target cell using a viral vector. The viral vector may be any virus which can serve as a viral vector. Suitable viruses are those which infect the target cells, can be propagated in vitro, and can be modified by recombinant nucleotide technology known in the art. Thus, in one aspect, the invention provides a viral vector comprising a nucleic acid sequence encoding a nucleic acid inhibitor of miR-9 (as described above), for use in the prevention or treatment of cystic fibrosis in a subject. Viral vectors suitable for use in the present invention include poxvirus vectors (such as non-replicating poxvirus vectors), adenovirus vectors, and adeno-associated virus (AAV) vectors. As used herein, a "non-replicating viral vector" is a viral vector which lacks the ability to productively replicate following infection of a target cell. Thus, the ability of a non-replicating viral vector to produce copies of itself following infection of a target cell (such as a human target cell in an individual undergoing vaccination with a non-replicating viral vector) is highly reduced or absent. Such a viral vector may also be referred to as attenuated or replication-deficient. The cause can be loss/deletion of genes essential for replication in the target cell. Thus, a non-replicating viral vector cannot effectively produce copies of itself following infection of a target cell. Non-replicating viral vectors may therefore advantageously have an improved safety profile as compared to replication-competent viral vectors. A non-replicating viral vector may retain the ability to replicate in cells that are not target cells, allowing viral vector production. By way of example, a non-replicating viral vector (e.g. a non-replicating poxvirus vector) may lack the ability to productively replicate in a target cell such as a mammalian cell (e.g. a human cell), but retain the ability to replicate (and hence allow vector production) in an avian cell (e.g. a chick embryo fibroblast, or CEF, cell). In some embodiments, the non-replicating poxvirus vector is selected from: a Modified Vaccinia virus Ankara (MVA) vector, a NYVAC vaccinia virus vector, a canarypox (ALVAC) vector, and a fowlpox (FPV) vector. MVA and NYVAC are both attenuated derivatives of vaccinia virus. Compared to vaccinia virus, MVA lacks approximately 26 of the approximately 200 open reading frames. In some embodiments, the adenovirus vector is a non-replicating adenovirus vector (wherein non-replicating is defined as above). Adenoviruses can be rendered non-replicating by deletion of the E1 or both the E1 and E3 gene regions. In some embodiments, the adenovirus vector is selected from: a human adenovirus vector, a simian adenovirus vector, a group B adenovirus vector, a group C adenovirus vector, a group E adenovirus vector, an adenovirus 6 vector, a PanAd3 vector, an adenovirus C3 vector, a ChAdY25 vector, an AdC68 vector, and an Ad5 vector.

According to the invention, the nucleic acid miR-9 inhibitor is administered to the subject using any suitable method that enables the nucleic acid miR-9 inhibitor to reach the lungs. The nucleic acid miR-9 inhibitor (as described above) may be administered to a subject by any suitable means known in the art. In some embodiments, the nucleic acid miR-9 inhibitor (as described above) is administered to the subject systemically (i.e. via systemic administration). Thus, in some embodiments, the nucleic acid miR-9 inhibitor (as described above) is administered to the subject such that it enters the circulatory system and is distributed throughout the body. In some embodiments, the nucleic acid miR-9 inhibitor (as described above) is administered to the subject by local administration, for example by local administration to the lungs.

In some embodiments, the nucleic acid miR-9 inhibitor is delivered by any device adapted to introduce one or more therapeutic compositions into the upper and/or lower respiratory tract. The devices may be adapted to deliver the therapeutic compositions of the invention in the form of a finely dispersed mist of liquid, foam or powder. The device may use a piezoelectric effect or ultrasonic vibration to dislodge powder attached on a surface such as a tape in order to generate mist suitable for inhalation. The devices may use any propellant system known to those in the art including, but not limited to, pumps, liquefied-gas, compressed gas and the like. Devices of the present invention typically comprise a container with one or more valves through which the flow of the therapeutic composition travels and an actuator for controlling the flow. The devices suitable for administering the constructs of the invention include inhalers and nebulizers. Various designs of inhalers are available commercially and may be employed to deliver the medicaments of the invention. These include the Accuhaler, Aerohaler, Aerolizer, Airmax, Autohaler, Clickhaler, Diskhaler, Easi-breathe inhaler, Fisonair, Integra, Jet inhaler, Miat-haler, Novolizer inhaler, Pulvinal inhaler, Rotahaler, Spacehaler, Spinhaler, Syncroner inhaler and Turbohaler devices. Thus, in some embodiments, the delivery is done by means of a nebulizer or other aerosolisation device provided the integrity of the nucleic acid miR-9 inhibitor is maintained.

The nucleic acid miR-9 inhibitor may be administered to the subject in a single delivery, such as a bolus delivery. Alternatively, the nucleic acid miR-9 inhibitor may be administered to the subject using a continuous delivery technique, such as a timed infusion. The nucleic acid miR-9 inhibitor may be administered using a repeated delivery regimen, for example on an hourly, daily or weekly basis. Nucleic acid miR-9 inhibitor dosages may be achieved by single or multiple administrations. By way of example, the nucleic acid miR-9 inhibitor may be administered to the subject in a regimen consisting of a single administration. Alternatively, the nucleic acid miR-9 inhibitor may be administered to the subject in a regimen comprising multiple administrations. For example, an administration regimen may comprise multiple administrations per day, or daily, weekly, bi-weekly, or monthly administrations. An example regimen comprises an initial administration followed by multiple, subsequent administrations at weekly or bi-weekly intervals. Another example regimen comprises an initial administration followed by multiple, subsequent administrations at monthly or bi-monthly intervals. Alternatively, administration of the nucleic acid miR-9 inhibitor can be guided by monitoring of CF symptoms in the subject. Thus, an example regimen comprises an initial administration followed by multiple, subsequent administrations carried out on an irregular basis as determined by monitoring CF symptoms in the subject. Methods for delivering nucleic acids are known in the art and will be familiar to a skilled person. By way of example, suitable nucleic acid delivery methods include ionophoresis, microspheres (e.g. bioadhesive microspheres), nanoparticles, dendritic polymers, liposomes, hydrogels, cyclodextrins, and proteinaceous vectors.

By a "therapeutically effective amount" of the nucleic acid miR-9 inhibitor as above described is meant a sufficient amount of the inhibitor to reach a therapeutic effect. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific inhibitor used; and like factors well-known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

For administration to a subject, the nucleic acid miR-9 inhibitor (or a viral vector encoding said nucleic acid miR-9 inhibitor) may be formulated as a pharmaceutical composition comprising a nucleic acid miR-9 inhibitor (as described above) or a viral vector (as described above) (as active ingredient). Such a pharmaceutical composition can be formulated according to known methods for preparing pharmaceutical compositions, such as by combining a nucleic acid miR-9 inhibitor or viral vector with a pharmaceutically acceptable carrier. Non-limiting examples of pharmaceutically acceptable carriers including water, saline and phosphate-buffered saline. The pharmaceutical composition in addition to a pharmaceutically acceptable carrier can further be combined with one or more of salt, excipient, diluent, albumin, immunoregulatory agent and/or antimicrobial compound. Pharmaceutically acceptable salts include acid addition salts formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Suitable excipients are, for example, water, saline, dextrose, glycerol, ethanol, or the like and combinations thereof. In addition, if desired, the pharmaceutical compositions may contain minor amounts of auxiliary substances such as wetting or emulsifying agents, and/or pH buffering agents. Examples of buffering agents include, but are not limited to, sodium succinate (pH 6.5), and phosphate buffered saline (PBS; pH 6.5 and 7.5). Thus, in one aspect, the invention provides a pharmaceutical composition comprising a nucleic acid miR-9 inhibitor (as described above) or a viral vector (as described above) and a pharmaceutically acceptable carrier. The pharmaceutical composition may contain 5% to 95% of nucleic acid miR-9 inhibitor or viral vectors, such as at least 10%, at least 25%, at least 40%, or at least 50, 55, 60, 70 or 75%.

The invention will be further illustrated by the following figures and examples. However, these examples and figures should not be interpreted in any way as limiting the scope of the present invention.

FIGURES

Figure 1:
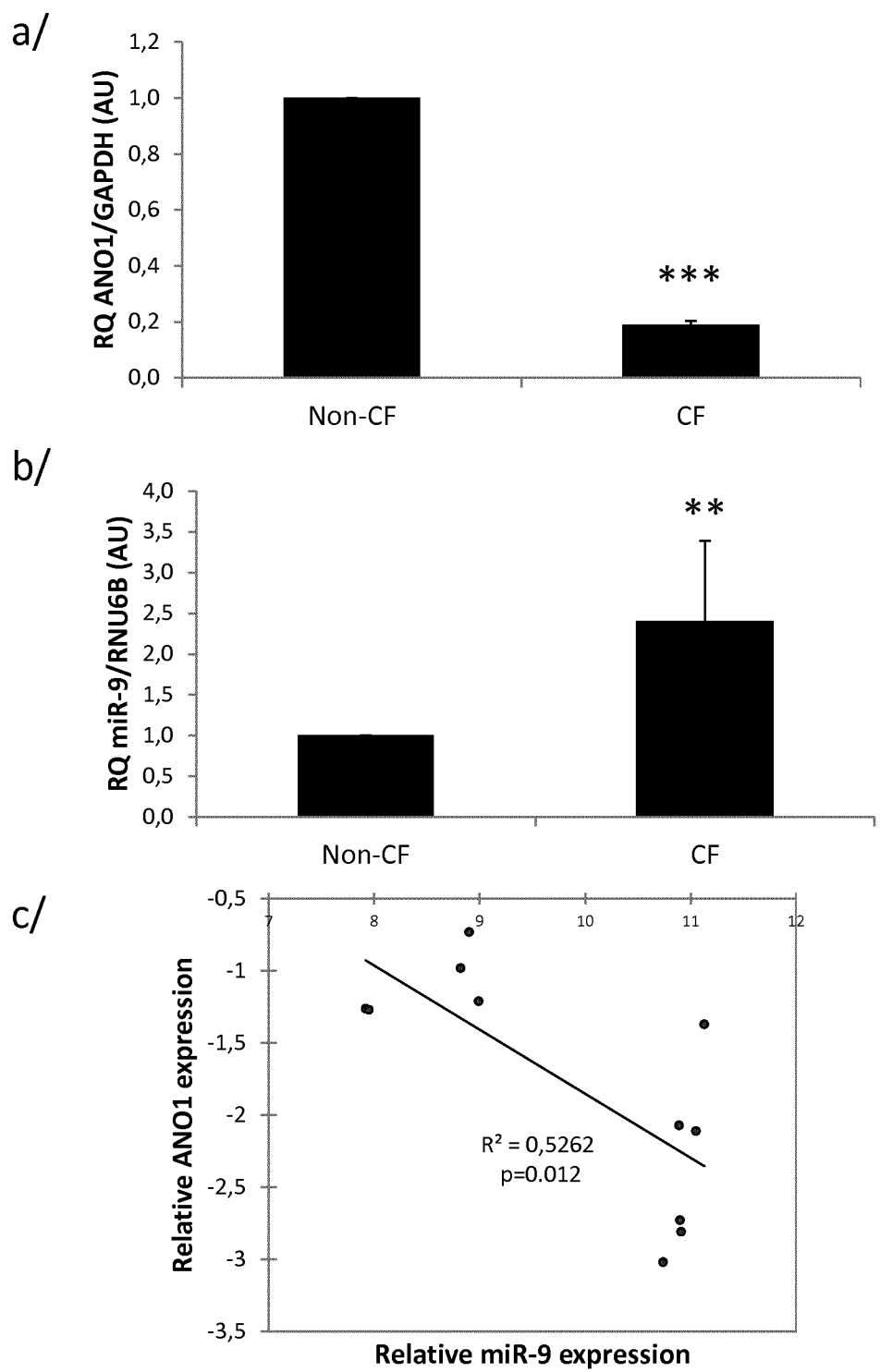

FIG. 1: Down-regulation of ANO1 mRNA and up-regulation of miR-9 are correlated in human bronchial epithelial cell lines. a/ Relative expression levels of ANO1 mRNA in non-CF (16HBE14o-; n=5) and CF (CFBE41o-; n=6) human bronchial epithelial cells. Data are quantified by qRT-PCR and are represented as fold change compared with normalized controls. b/ miR-9 expression in non-CF and CF bronchial epithelial cell lines measured by qRT-PCR. Relative expression levels were normalized to RNU6B. Data are represented as mean+/−SD and were compared by t test. All qRT-PCR experiments were performed in triplicate. c/ Negative correlation between miR-9 and ANO1 mRNA expression levels in non-CF and CF bronchial epithelial cell lines (Pearson's correlation analysis p=0.012).

Figure 2:
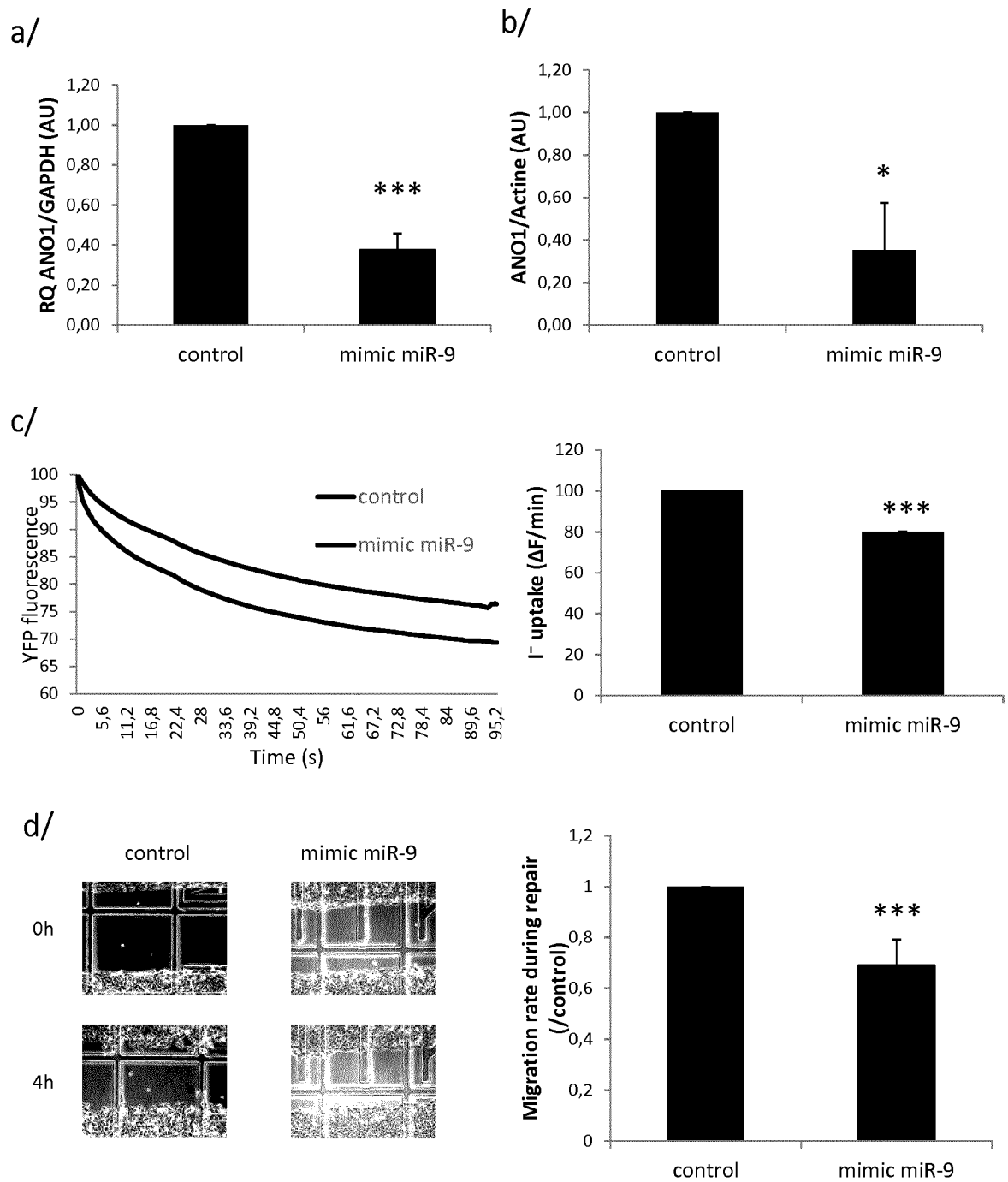

FIG. 2: miR-9 regulates ANO1 expression, ANO1 chloride activity and migration rate of non-CF cells. Non-CF cells (16HBE14o-) were transfected with a mimic of miR-9 (30 nM) or a negative control during 48 h. a/ ANO1 mRNA expression was analyzed by RT-qPCR and normalized to GAPDH (n=3). b/ ANO1 protein expression was analyzed by western-blot using anti-ANO1 antibody and normalized to β-actin (n=3). c/ ANO1 chloride channel activity assessed by I⁻ quenching of halide-sensitive YFP-H148q/I152L protein. Representative and original traces of ANO1 chloride activity (left) and quantification (right) of non-CF cells transfected with a mimic of mir-9 or negative control (n=8 in triplicate). d/ Representative images taken during 4 h of wound closure of non-CF cells transfected with a mimic of miR-9 or a negative control (left) and quantification of migration rates during repair (n=5).

Figure 3:
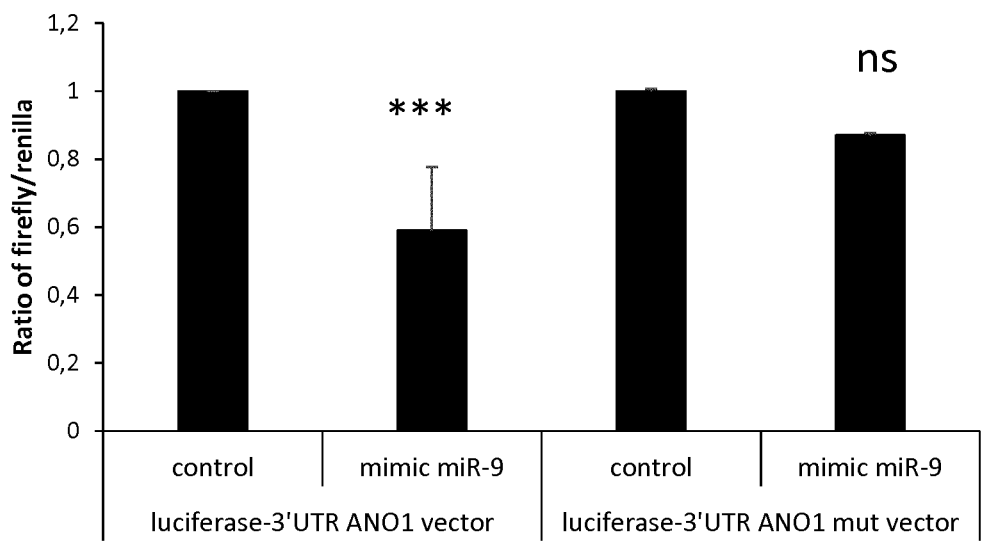
Figure 3:
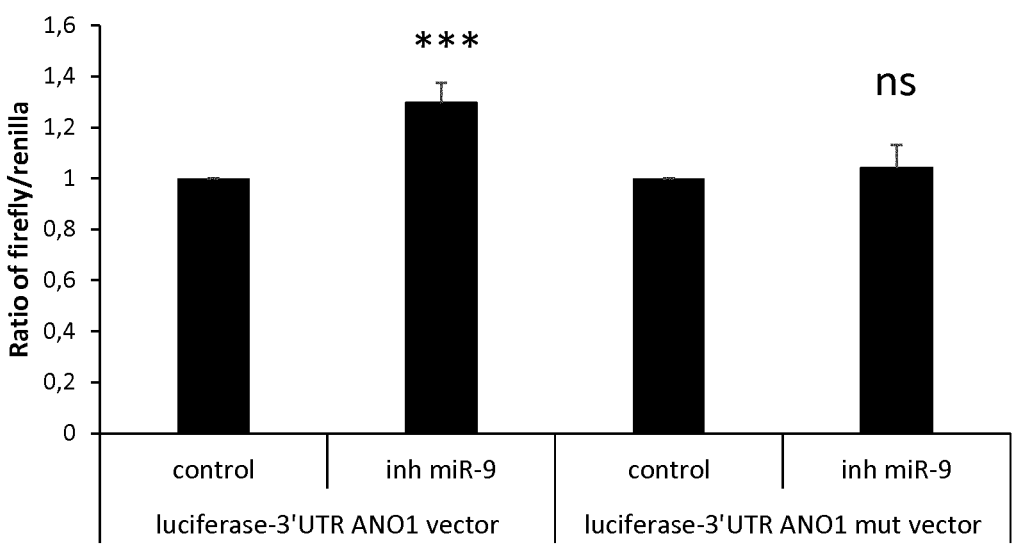

FIG. 3: miR-9 directly target ANO1 3'UTR in non-CF and CF cells. a/ Relative luciferase activity in non-CF cells (16HBE14o-) transiently transfected with a luciferase-3'UTR ANO1 vector or a luciferase-3'UTR ANO1 vector mutated for miR-9 binding sites and co-transfected with a mimic of miR-9 (mimic miR-9) or a negative control (control). Firefly luciferase activity was normalized to the Renilla luciferase activity (n=3 with 8 replicates). b/ Relative luciferase activity in CF cells (CFBE41o-) transiently transfected with a luciferase-3'UTR ANO1 vector or a luciferase-3'UTR ANO1 vector mutated for miR-9 binding sites and co-transfected with an inhibitor of miR-9 (in miR-9) or a negative control (control). Firefly luciferase activity was normalized to the Renilla luciferase activity (n=3 with 8 replicates). Histograms represent the average value+/−SD and were compared by t test.

Figure 4C:
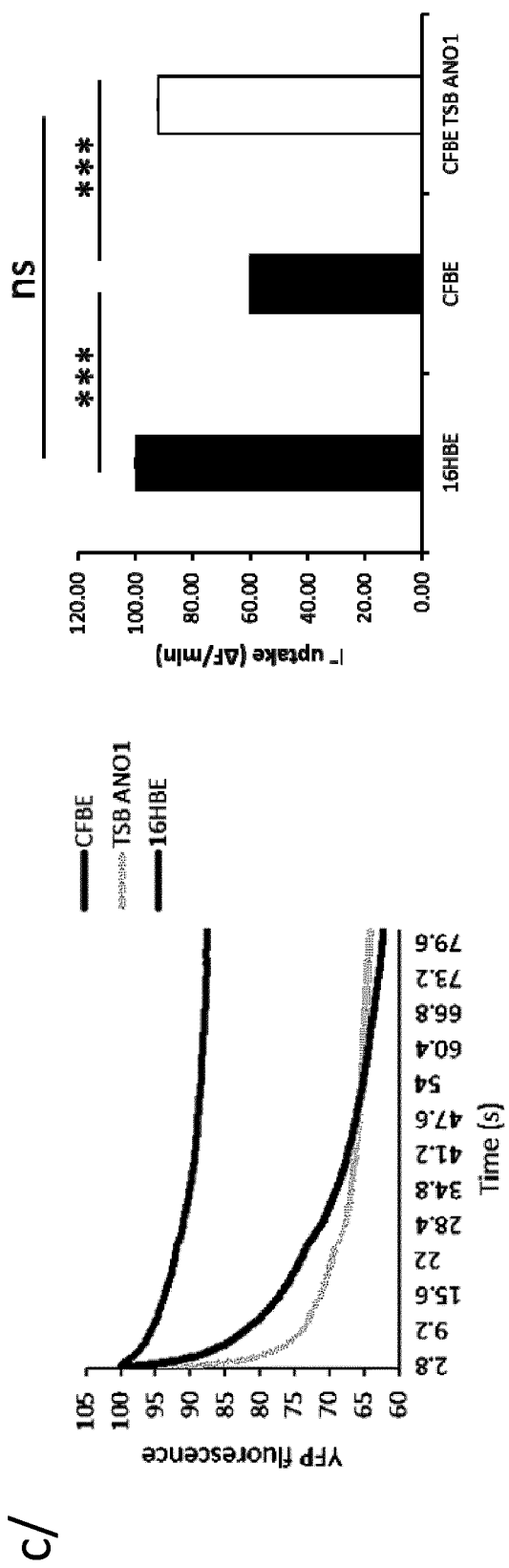
Figure 4D:

FIG. 4: Specific TSB allows to increase ANO1 expression, chloride activity and migration rate of CF cells. CF cells (CFBE41o-) were transfected with a control LNA (control) or ANO1 TSB during 24 h. a/ ANO1 protein expression was analyzed and quantified by western-blot using anti-ANO1 antibody and normalized to β-actin (n=4). b/ Kinetic of YFP-H148Q/I152L protein quenching after injection of I− in the medium. 24 h After transfection with YFP-H148Q/I152L plasmid cells are selectively microinjected with the control or ANO1 TSB as indicated in the images. Scale bar 5 µm. c/ Representative and original traces of ANO1 chloride activity (left) and quantification (right) of CF bronchial epithelial cells transfected with ANO1 TSB or a negative control (n=8 in triplicate) and compared to non-CF cells (16HBE14o-). d/ Migration rates during repair of CF cells. Representative images were taken during 4 h of wound closure of CF cells (left) and quantification (right) (n=5). Scale bar 10 µm. Histograms represent the average value+/−SD and were compared by t test.

Figure 5E:
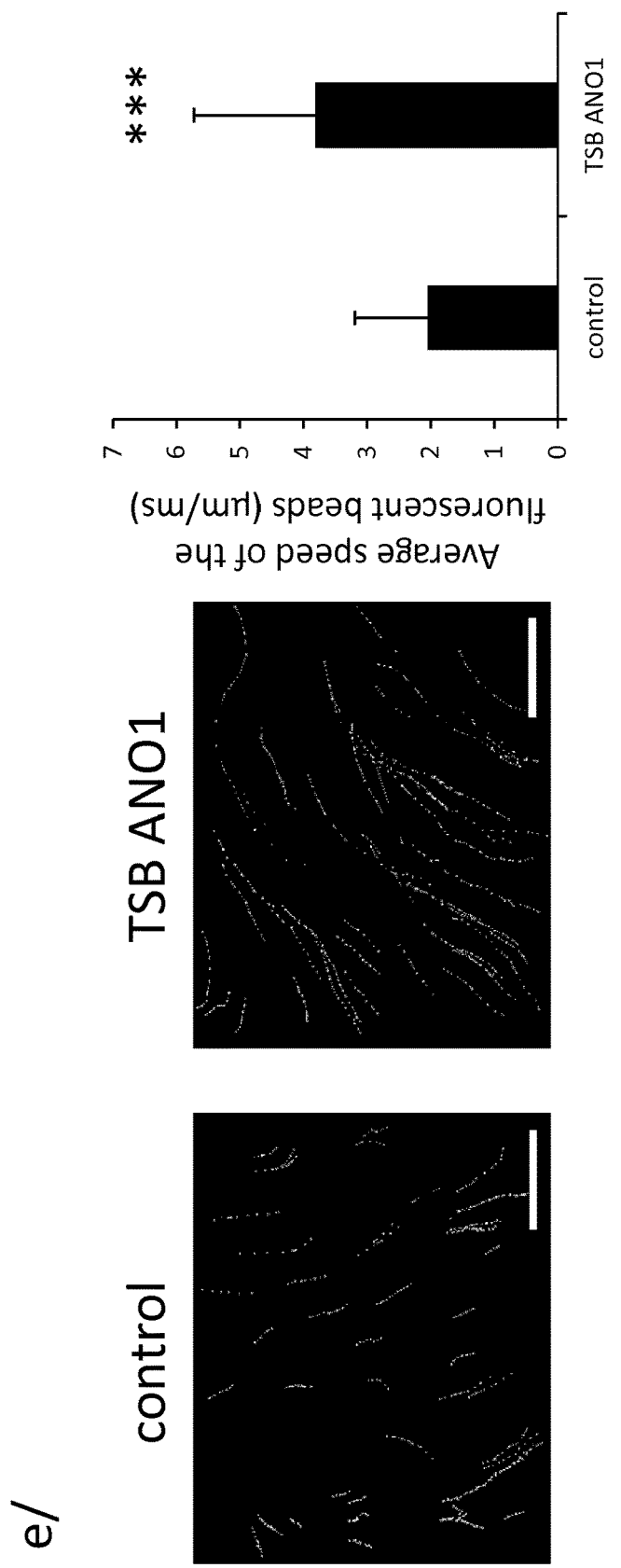

FIG. 5: Specific TSB allows to increase ANO1 expression, chloride activity and migration rate of primary CF cells. Primary human bronchial epithelial cells (hAECB) and fully differentiated human bronchial air-liquid-interface cultures, isolated from bronchial biopsies from CF (F508del/F508del) patients were transfected with a control LNA (control) or ANO1 TSB every day during 3 days: a/ Confocal microscopic analysis of TSB fluorescein-conjugated transfected in the human bronchial cells isolated from CF patient (green). The nucleus was stained with DAPI (blue) and merged images are shown. Scale bars 10 µm. b/ ANO1 protein expression was analyzed and quantified by western-blot using anti-ANO1 antibody and normalized to β-actin (n=6). c/ Representative and original traces of ANO1 chloride activity (left) and quantification (right) of hAECB CF cells transfected with ANO1 TSB or a negative control (n=4). d/ Migration rates during repair of primary CF cells. Representative photographs were taken during 4 h of wound closure of CF cells (left) and quantification (right) (n=4). Scale bar 20 µm. e/ Effect of control or ANO1 TSB on mucus dynamics after 30 days of transfection. The movements of 100 beads were quantified for each condition and the average speed in µm/ms were determined. Scale bar 40 µm. Histograms represent the average value+/−SD and were compared by t test.

FIG. 6: Use of specific TSB is well tolerated in mice and increases ANO1 chloride activity in CF mice. a/ Representative and original traces of ANO1 chloride activity (left) and quantification (right) of MLE15 cells transfected with a control LNA (control) or ANO1 TSB. b/ Plan of the experiment for CF mice. Intranasal instillation of a control or ANO1 TSB were done at days 7 and 14 after reception and mice were sacrificed at day 21. c/ Growth curves of mice from the day of the reception. Arrows represent intranasal instillation. d/ Representative and original traces of ANO1 chloride activity (left) and quantification (right) of cells isolated from CF mice instilled with ANO1 TSB or a negative control.

Figure 7:
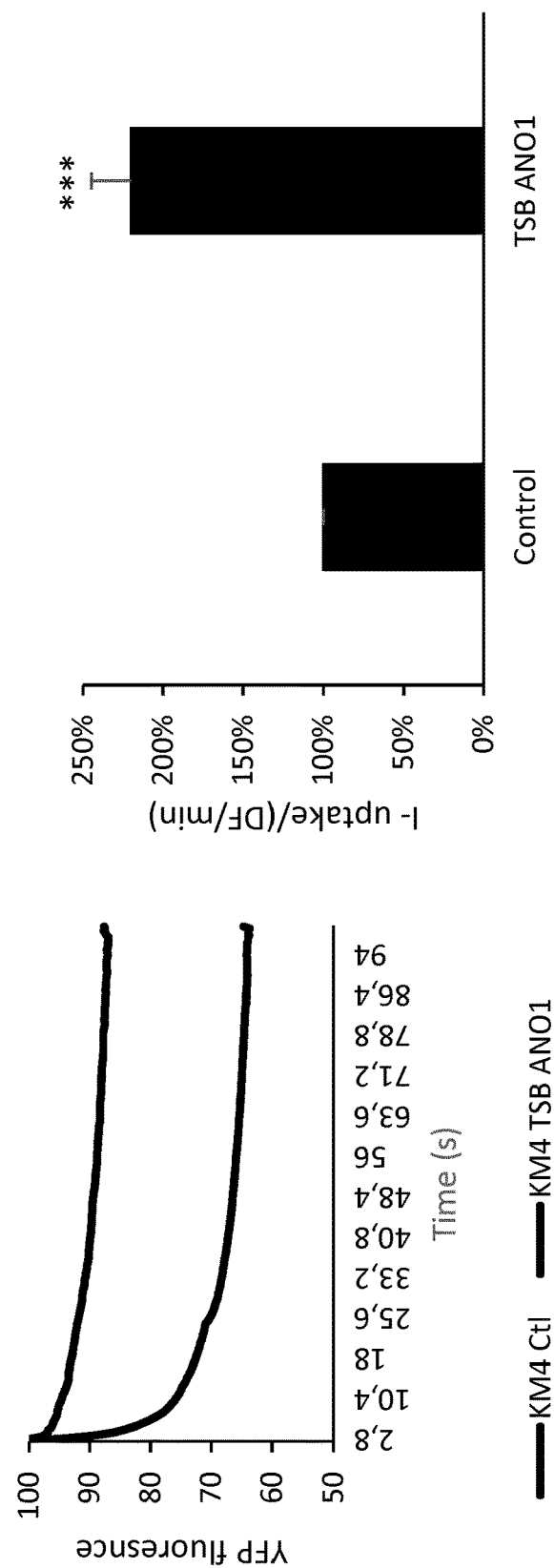

FIG. 7: Specific TSB increases ANO1 chloride activity of human cystic fibrosis bronchial gland cells. Human cystic fibrosis bronchial gland cells (KM4) were transfected with a control LNA (control) or ANO1 TSB during 24 h. Representative and original traces of ANO1 chloride activity (left) and quantification (right) of CF bronchial gland cells. Quantification was obtained from 3 differents experiments with 24 wells/experiment/condition.

Figure 8:
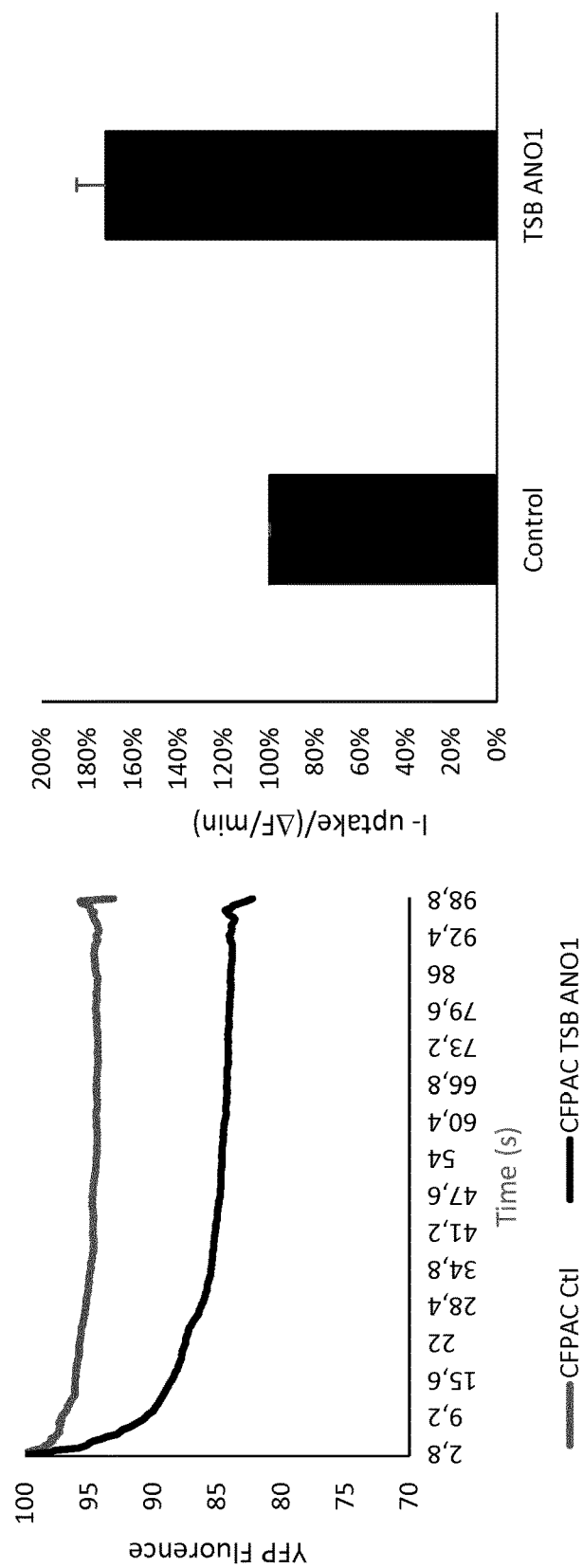

FIG. 8: Specific TSB increases ANO1 chloride activity of cystic fibrosis pancreatic cell line. CF cells (CFPAC1) were transfected with a control LNA (ctl) or a ANO1 TSB during 24 h. Representative and original traces of ANO1 chloride activity (left) and quantification (right) of CF pancreatic cell line. Quantification were obtained of 3 different experiments with 24 wells/experiment/condition.

EXAMPLE

Material & Methods

Bioinformatics Analysis of miRNAs Targets Genes

The role of miRNAs in the regulation of ANO1 expression has been examined using computational studies showed that the 3' UTR of ANO1 is predicted to contain numerous seed regions recognized by a variety of miRNAs. The putative miRs predicted for ANO1 mRNA were identified and compared using the online target prediction algorithm: Targetscan (targetscan.org), Pictar (pictar.mdc-berlin.de), miRDB (mirdb.org/miRDB) and miRANDA (microrna.org). NCBI and Ensembl genome browsers (ensembl.org/index.html) provided information of human ANO1 gene (NM_018043; ENST00000355303).

Cell Culture

The human bronchial epithelial cell lines 16HBE14o-(non-CF) and CFBE41o-(CF) were obtained as a gift from Dr. D. C. Gruenert (San Francisco, Calif., USA) and cultured in MEM containing 10% bovine growth serum and 1% penicillin/streptomycin. Cells cultures were grown and maintained at 37° C. in a 5% CO2 humidified incubator. Primary human bronchial epithelial cells (hAECB) are fully differentiated human bronchial air-liquid interface cultures (MucilAir™), isolated from bronchial biopsies from CF (F508del/F508del) patients, were purchased from Epithelix SARL (Geneva, Switzerland) and cultured according to the provider's recommendations.

Cell Transfection: Mimic, Inhibitor and Target Site Blocker

Non-CF and CF cell lines were transfected with miR-9 mimic, miR-9 inhibitor or negative control (Thermo Fischer Scientific, France) using HiPerfect (Qiagen, France) at 30 nM according to the manufacturer's instructions. Forty-eight hours after transfection, cells were lysed for miRNAs and RNAs extraction or proteins extraction. CF cell lines were transfected with LNA-enhanced oligonucleotides designed to overlap miR-9 target site in ANO1 3'UTR (ANO1 TSB) or with a miRCURY LNA (Locked Nucleic Acid) microRNA inhibitor negative control (LNA control) (Exiqon, Denmark) using Interferin (Polyplus, Ozyme, France). 24 h after transfection, cells were lysed for proteins extraction, or experiments were performed for chloride activity or migration assays. hAECB cells were transfected adding medium containing LNA control or TSB ANO1 without any transfection reagent to the upper compartment of ALI (Air-Liquid Interface) cells. After 2 h at 37° C., the medium was removed from the upper compartment to restore the ALI condition. Freshly prepared LNA control or TSB ANO1 were added every day for three days and ANO1 expression, ANO1 chloride activity and migration were assessed 24 h post-treatment.

Luciferase Assay

For these experiments, we used the ANO1-3'UTR-pMir-Target Vector luciferase plasmid (Origene Technologies, Rockville, USA) and a mutated ANO1 3'UTR-pMir vector mutagenized in the seed region of miR-9 (MIMAT0000441). CF and non-CF cells were seeded in 24-well plates and were transfected next day with 0.5 μg pMir vector and 0.1 μg Renilla luciferase vector using Exgen 500 (Euromedex, France). Cells were cotransfected with 30 nM mimic of miR-9, an inhibitor of miR-9 or a negative control (Thermo Fischer Scientific, France). Lysates were prepared 48 h hours after transfection and assayed for both Firefly and Renilla luciferase using luciferase assay system (Promega, France). Firefly luciferase activity was normalized to the Renilla luciferase activity.

RNAs and miRNAs Extraction and Quantitative RT-PCR (qRT-PCR) Analysis

RNAs and miRNAs were extracted using Macherey-Nagel kit (Duren, Germany). Reverse Transcription (RT) for human miR-9 and RNU6B were carried out with TaqMan MicroRNA Assay kit (Thermo Fischer Scientific) using 20 ng miRNAs sample. RT for ANO1 and GAPDH were done using High Capacity cDNA Reverse Transcription kit (Thermo Fischer Scientific) using 1 μg RNA sample. Quantitative PCR was performed using an ABI StepOnePlus™ (Thermo Fischer Scientific) and TaqMan technology. For relative quantification, the ANO1 mRNA level, calculated using the 2-ΔΔCt method was normalized to GAPDH and the expression levels of respective non-CF models and miR-9 level was normalized for RNU6B. Each sample was assessed in triplicate to ensure experiment quality.

Western-Blot Analysis

As previously detailed, 20 μg of total proteins extract was reduced and size-separated on 8% SDS-polyacrylamide gels then transferred to PVDF membranes (Bio-Rad, Marnes-la-Coquette, France), blocked in 5% BSA (PAA, Les Mureaux, France). Next, the membranes were incubated with specific primary antibodies against ANO1 (Abcam, Paris, France) and β-actin (Sigma, Saint Quentin Fallavier, France). The proteins of interest were detected, imaged, and quantified as previously described.

Migration Assays

Migration assays were performed using specific wound assays chambers (Ibidi, Biovalley, Marne la Vallée, France) that provided uniform wounds between two monolayers. A constant number of cells producing a confluent layer within 72 h were seeded in each well of Ibidi® silicone culture-inserts. The cells were incubated at 37° C. and 5% CO2. After 24 h, cells were transfected with a mimic of miR-9 or a negative control (Life Technologies, Saint Aubin, France) or a TSB ANO1/LNA control (Exiqon). The culture insert was removed 48 h later, leaving a cell-free gap (or wound) for cell colonization. For hAECB cells, wounds were done using a tip soaked in liquid nitrogen. Wound closure was observed for 4 h under an Axiovert 200 microscope with a chamber to maintain 37° C. and 5% CO2. Mean migration rates during wound closure were assessed in three areas of the gap. At each time point and in each field, five lengths were measured using AxioVision Rel software (Zeiss).

ANO1 Chloride Activity

ANO1 Cl− activity was assessed by I− quenching of halide-sensitive YFP-H148Q/I152L protein (Thermo Fischer Scientific). The probe was transfected into the cells and, after 48 h of culturing, conductance was stimulated with UTP (10 μM). I− solution (140 mM) was added, and fluorescence was recorded into a plate reader as previously described. The initial I− influx rate following the addition of each solution was computed from changes in YFP fluorescence data using non-linear regression and represents the original and representative traces. For quantitative analysis, the slope for fluorescence quenching was performed using a linear regression and correlates to the size of the chloride conductance (I− uptake). The rate of change (ΔF/min) is used for bar graph representation.

Microinjection Experiments

Cells were seed on Ibidi Dishes with bottom glass 24 h after transfection by halide-sensitive YFP-H148Q/I152L protein, ANO1TSB or control TSB were microinjected in CF cells using Xenowork micromanipulator and digital microinjector (Sutter Instrument, CA, USA). To discriminate the different transfection, ANO1 TSB was microinjected with Dextran Texas Red neutral (Thermo Fischer Scientific). 4 h after microinjection, activation of cells by I⁻ were performed by a microperfusion system (Valvelink from Automate Scientific, CA, USA) and were recorded with an x63 objective lens on an Axiovert 200 microscope (Zeiss). Quantification was performed with ImageJ software (US National Institutes of Health, ML, USA).

Animals

All experiments were performed in accordance with our Institutional Animal Care and Use Department (approval 20150511145844v3 of the Ethical Committee for Laboratory Animal Care Charles Darwin France). The study was carried out on CF male mouse model $Cftr^{tm1Eur}$ mice homozygous for the F5058del mutation in the 129/FVB outbreed background F508del-CFTR and their normal littermates. Animals were maintained in the Specific Pathogen Free mouse facility of Paris 6 with access to food and water ad libitium and weight was recorded every day. Mice were obtained form CDTA-CNRS (Orléans, France) after weaning at 8 weeks of age. To minimize bowel obstruction a commercial available osmotic laxative containing polyethylene glycol (PEG-3350) and electrolytes (Movicol®) was continuously supplied at 6% in the drinking water[10]. Prior to instillation, mice were anesthetized with 2.5% isoflurane delivered in O2 (2 L/min). Intranasal administration of each challenge dose (one per week during 2 weeks) of TSB (10 mg/kg) was performed by pipetting the solution onto the outer edge of each nare of the mice. Mice receiving isoflurane anesthesia were removed from the induction chamber, and instillation was performed immediately. After 7 days of last challenge, mice were sacrificed by a lethal dose of CO2. After exsanguination, the chest wall was opened and the trachea isolated. Premo Halide sensor was performed on a section of the trachea according to the manufacturer's instructions, and chloride activity was recorded as previously described.

Statistical Analysis

All data are described as mean±SD. In the figure legends, n indicates the number of repeated experiments. Between-group differences were tested using the Student t-test. Values of p lower than 0.05 were considered significant; in the figures, statistically significant differences with p<0.05 (*), p<0.01 (), and p<0.001 (*) are indicated.

Results

Down-regulation of ANO1 and up-regulation of miR-9 are correlated in human bronchial epithelial cell lines We previously showed that ANO1 expression and activity were decreased in the CF context compared to non-CF, but the mechanisms involved in these decreases are still unknown. We are interested in microRNAs (miRNAs) which are small non-coding RNA regulating gene expression post-transcriptionally. So, we used several databases with different algorithms: Targetscan, miRDB, miRANDA and Pictar to predict miRNAs which could target ANO1 and we found that four miRNAs were predicted to target ANO1: miR-9; miR-19a; miR-19b and miR-144. After preliminary experiments, we focused our attention on miR-9, and the others results were included in the supplemental data of the article. The expression of miR-9 was studied by qRT-PCR using TaqMan miRNA assays and was found to be increased in CF bronchial epithelial cell lines compared to non-CF (CFBE41o-versus 16HBE14o-) in contrast to ANO1 expression (FIGS. 1a and 1b). Interestingly, using the Pearson's correlation test, we demonstrated that ANO1 transcripts were significantly associated with miR-9 expression levels (p=0.012) (FIG. 1c).

miR-9 Regulates ANO1

The increase expression of miR-9 in CF cells led us to hypothesize that ANO1 is a direct target of miR-9. So we have transfected non-CF cells (16HBE14o-) with a mimic of miR-9, and we have verified the transfection efficiency by RT-PCR and using the Smartflare method to miR expression (see supplemental data of the article). We also verified that miR-9 overexpression following the mimic of miR-9 transfection is specific quantifying others miRs (miR-19a for example, supplementary data). Next, the effects of miR-9 overexpression on ANO1 mRNA and protein was assessed. Non-CF cells were transfected with miR-9 mimic or a negative control. Consequently to the transfection, FIG. 2a shows that miR-9 overexpression (mimic miR-9) significantly decreased ANO1 mRNA expression by an average of 60% in 16HBE14o- cells. ANO1 protein expression examined by Western blot and immunocytochemistry was also significantly decreased after transfection of miR-9 mimic (FIG. 2b). We thus concluded that miR-9 regulated ANO1 expression.

miR-9 Regulates ANO1 Chloride Activity and Migration Rate of Cells

Subsequently, we wanted to assess the effects of miR-9 overexpression on ANO1 chloride activity. FIG. 2c shows that miR-9 overexpression leads to a decrease ANO1 chloride activity. We also studied the effects of miR-9 presence on migration rate since it has been demonstrated previously by our group that ANO1 is involved in cell migration. FIG. 2n shows that miR-9 overexpression significantly decreases the migration rate of non-CF cells. These results show that miR-9 allows to change ANO1 chloride activity and migration rate of cells.

miR-9 Directly Regulates ANO1

To test whether miR-9 represses ANO1 expression by binding to its' 3'UTR, 16HBE14o- cells were transfected with a luciferase reporter vector containing WT ANO1 3'UTR (WT-ANO1-3'UTR) or a negative control reporter with mutations in the predicted binding sites for miR-9 (mut-ANO1-3'UTR). Cotransfection with miR-9 mimic resulted in significant decrease in luciferase gene expression from WT-ANO1-3'UTR compared with mut-ANO1-3'UTR demonstrating direct miR-9-ANO1 interaction in non-CF cells (FIG. 3a). We have done the same experiment using an inhibitor of miR-9 in CFBE41o⁻ cells (FIG. 3b), and we observed a significant increase in luciferase activity when CF cells are transfected with the inhibitor of miR-9 compared to the control whereas no significant difference was observed with the mutated plasmid. We thus concluded that miR-9 directly regulates ANO1 in CF cells.

Use of Specific TSB Allows Increasing ANO1 Expression, Chloride Activity and Migration Rate of CF Cells In the context of CF, it would be interesting to increase ANO1 expression to increase ANO1 chloride activity. As miR-9 has many targets in cells, inhibitors of miR-9 are not specific so we designed a specific target site blocker (TSB ANO1) which will bind ANO1 3'UTR and prevent miR-9 fixation. We have transfected CF cells with control or TSB ANO1 during 24 h and after we have quantified ANO1 protein expression and we have observed that ANO1 protein expression significantly increases when cells are transfected with TSB ANO1 (FIG. 4a). By microinjection experiments associated with microscopy, we can observe in the same field a single cell microinjected with the TSB control and another cell microinjected with ANO1 TSB (FIG. 4b). In this approach, the decreased fluorescence associated with the chloride efflux is completely different in the two cells. More, by a more classical method, we also quantified ANO1 chloride activity using the Premo Halide sensor method and remarkably we observed a significant increase in ANO1 chloride activity when cells are transfected with ANO1 TSB (FIG. 4c). It is interesting to note that in this case when cells are transfected with ANO1 TSB, we observed the same chloride activity as non-CF cells. Finally, we looked at migration, and we found a significant increase in migration rate of cells when cells are transfected with ANO1 TSB compared to the control.

Use of Specific TSB Allows to Increase ANO1 Expression, Chloride Activity and Migration Rate of Primary CF Cells To mimic in vivo epithelium, we decided to transfect primary human bronchial epithelial cells (hAECB) and fully differentiated human bronchial air-liquid interface (ALI) cultures isolated from bronchial biopsies from CF (F508del/F508del) patients with control or the TSB ANO1. We successfully transfected the cells adding medium containing the TSB ANO1 or control without any transfection reagent to the apical face of ALI cells (FIG. 5a). After 2 h at 37° C., the medium was removed from the apical face to restore the ALI conditions. Freshly prepared control oligonucleotides or TSB ANO1 were added during three days, and the effects of transfection were observed 24 h post-treatment. The results of western blot showed that we significantly increase ANO1 expression when primary cells are transfected with ANO1 TSB compared to the control (FIG. 5b). Furthermore, after transfection, we observed a significant increase in ANO1 chloride activity (FIG. 5) and migration rate (FIG. 5d) of primary CF cells with ANO1 TSB. We have also looked at ciliary beat frequency using fluorescent beads and interestingly we have observed an increase in the average speed of the beads with ANO1 TSB. Utilization TSB ANO1 in primary cells allows modulating deficient parameters of CF cells by improving ANO1 chloride activity, migration rate of cells and the ciliary beat frequency.

Discussion:

In this study, we present the first report, to our knowledge, on a direct correlation between miRNA and ANO1 expression, especially in CF. Thus, we found that miR-9 is significantly overexpressed in CF bronchial epithelial cells, and miR-9 directly regulates ANO1. Using a target site blocker, specially designed to prevent miR-9 fixation on ANO1 3'UTR mRNA (ANO1 TSB), we have shown that we are able to increase ANO1 expression and ANO1 chloride activity in CF cell lines, in CF primary cells cultured in an air-liquid interface but also in CF mice. It is interesting to note that, when cells were transfected with ANO1 TSB, we have the same level of chloride activity as in non-CF cells. We have studied ANO1 regulation by miR-9 using a candidate gene approach based on in silico analysis. We have looked at predictions from several miRNA-target interaction algorithms and focus on their intersection. Four miRNAs were strongly predicted to target ANO1 mRNA: miR-9; miR-19a; miR-19b and miR-144. After preliminary experiments, we observed that miR-19a and miR-19b do not regulate ANO1 and that miR-144 regulates ANO1 but not directly (supplemental data of the article). For example, we hypothesized that miR-144 could regulate ANO1 activity via CFTR interaction, but this result needs to be more investigated. Indeed, some studies have already shown that miR-144 regulates CFTR, and another study has shown that there exists a co-localization between CFTR and ANO1 even if an interaction remains unclear. In this study, we gained insight into miR-9 overexpression in CF cells compared to non-CF and, more, we have demonstrated that miR-9 and ANO1 levels of expression are correlated in CF and non-CF cells. We thus validated ANO1 as a target of miR-9 using a unique strategy to demonstrate that decreased ANO1 expression in CF cells is caused by ANO1 repression by miR-9 but how the mutation in CFTR induce miR-9 deregulation in CF remains unknown. Galietta et al. have previously shown that ANO1 expression is stimulated by IL-4[11], so we have stimulated our cells by IL-4 to see if there change miR-9 expression, but there is no difference between the conditions unstimulated and IL-4 stimulation (data not shown).

Together, our results provide evidence that miRNA targeting ANO1 mRNA can be considered as potential therapeutic target in CF, and TSB a real alternative. Since ANO1 had been discovered in 2008, this protein is considered as a therapeutic target in CF[12] since it is defined as a chloride channel but also because ANO1 is involved in others deregulated parameters in CF as HCO3−secretion, migration, and proliferation[7]. Furthermore, targeting ANO1 seems to be a promising target since it is independent of CFTR mutations, but no efficient drug therapy is available or suggested so far. In 1991, some groups discovered that uridine-5'-triphosphate can stimulate chloride secretion in CF respiratory epithelium[13]. This nucleotide activates a signal by binding to a purinergic receptor to release intracellular calcium and activate undefined CaCCs distinct from CFTR[14]. In vitro, CF tissue culture studies have demonstrated that UTP can restore liquid transport, enhance tracheal mucus viscosity, ciliary beat frequency, inhibit sodium absorption and increase airway hydration that should be beneficial in treating CF[15,16]. These promising results have allowed the development of new drugs called INS365 and INS37217 (later named Denufosol®). These drugs are more resistant to enzymatic degradation than UTP[17]. Based on these data, denufosol (Inspire Pharmaceuticals) was carried into clinical trials using nebulization for a delivery approach. After some promising results obtained in the first clinical trials, an international phase 3 clinical trial was completed including 466 patients. This trial has failed to demonstrate any benefit for CF patients and the company lost $400.000.000 in a single day. Beyond this results, many points could explain this outcome and were well detailed in an article by Pr. Moss from Stanford University School of Medicine[18]. First, the molecular identity of the CaCC has discovered after the Phase 3 trials, and exact effects of denufosol were only empiric and very transient. Thus, it is well admitted that administration of UTP to the apical surface of the epithelium binds to the P2Y2 receptor and causes a rapid increase in cytosolic free calcium concentration with a rise of chloride efflux within a second to some minutes[11]. Second, the stability of this drug in the context of CF remained very problematic with a very short half-life from 3-hour in nasal epithelium, 17 min in the lung of CF patients and 30 s in the blood due to nucleosidases[17,19]. Third, the key selection criteria for young CF patients (mean age 14.2 yr) with only mild or no appreciable baseline impairment of FEV1 (92% of predicted) to validate the efficacy of a drug could be discussed. In this case, many drugs demonstrated clinically beneficial endpoints for patients that do not improve FEV1[20,21]. However, while targeting CaCC holds promise, clinical benefits have not yet been achieved that is the reason why we have focused our study on a more objective drug approach.

Indeed, to be more accurate than antagomiR or RNA sponges approach to silence miRNA, we have used target site blockers (TSB) to block the target site(s) of miRNA(s) in the 3'UTR of ANO1 to avoid miRNA inhibition[9]. We studied the ANO1 regulation by miR-9 in CF cell lines and primary cultures obtained from F508del homozygous patients the most current mutation worldwide. In these cells, with the TSB ANO1, we succeed in increasing ANO1 expression, chloride activity, and cell migration. Interestingly, we observed an increase in migration rate of cells when we transfected CF cell lines and primary cultures differentiated in the air-liquid interface with TSB ANO1. Migration is a part of the repair process, so we hypothesize that treat CF patients with TSB ANO1 could improve bronchial epithelial repair. Our data highlight the therapeutic potential of use our target site blocker for the treatment of cystic fibrosis. The base of this strategy is innovative either in what it does, or how it does it, relative to therapy proposed to CF patients. By contrast to denufosol, we have used our knowledge of molecular biology to design a new and specific strategy to increase the expression of one specific target protein using miRNA. The challenge was to create a very specific molecule able to induce a strong activity of ANO1 even in a complex system as CF. After pondering it more, we have decided to use TSB modified with LNA for the stability and the specificity to control a gene expression. So, this approach is CFTR-mutation independent and the used of artificial miRNA target site are now emerging. Considering that CF is caused by more than 1900 different mutations, we have tried to determine a new target, independent from CFTR such as ANO1. Even if miRNA are stable on the various fluids in the human body[22,23], the degradation of the drug remains a crucial point in the case of CF context, since denufosol strategy failed. A valuable addition to the miRNA tools came from LNA (locked nucleic acid), a bicyclic high-affinity RNA analog in which the ribose ring is chemically locked in an N-type (C3'-endo) conformation. This modification is essential because LNA-modified oligonucleotides possess high thermal stability when hybridized with the mRNA target[24,25]. A locked nucleic acid (LNA)-based inhibitor of miR-122, Miravirsen is currently undergoing clinical trials for the treatment of hepatitis C viral infections. The role of the liver-specific miR-122 is somewhat unusual; instead of targeting the 3'UTR and causing signal repression, it binds to the 5'UTR of hepatitis C virus RNA and promotes its replication. The effects of Miravirsen have been tested on chimpanzees and have shown that LNA-modified anti-miRNA are accurate, non-toxic and very stable because it has been detected 8 weeks after the end of the treatment and until week 25. Furthermore, the effects of Miravirsen on HCV RNA levels were also prolonged at the end of the treatment[26]. For our study, Miravirsen's success serve as an inspiration and example to propose a potential clinical strategy in the case of CF. In our case, our TSB can correct the different parameters analyzed in the airways even in mice model. In our condition, we are able to observe an activation of chloride efflux seven days after the last instillation. The stability and the physiological activity is a key of our drug. Of course, the method of administration of the drug in the respiratory tract should be optimized to be used in CF patients.

The effort to develop drugs that activate chloride efflux for the treatment of cystic fibrosis pathology are ongoing but are limited by the different CFTR mutation present in CF patients. To our knowledge, this is the first demonstration that an alternative therapy is proposed to correct precisely an alternative chloride channel as ANO1. In the present study, the use of TSB targeting the seed region of miR-9 demonstrates the potential benefits of ANO1 therapy for the treatment of cystic fibrosis patients. The other major results of the present study are that short-term treatment targeting ANO1 is able to correct different phenotypic factors dysregulated in the epithelium of cystic fibrosis patients. We believe that this approach using TSB targeting ANO1 has the potential to provide an alternative treatment for CF patients. Taken together, these results highlight that a better understanding of physiology is essential for patients.

REFERENCES

Throughout this application, various references describe the state of the art to which this invention pertains. The disclosures of these references are hereby incorporated by reference into the present disclosure.

1. Pittman, J. E. & Ferkol, T. W. The Evolution of Cystic Fibrosis Care. *Chest* 148, 533-542 (2015).
2. Riordan, J. R., et al. Identification of the cystic fibrosis gene: cloning and characterization of complementary DNA [published erratum appears in Science 1989 Sep. 29; 245(4925):1437]. *Science* 245, 1066-1073 (1989).
3. Van Goor, F., et al. Rescue of CF airway epithelial cell function in vitro by a CFTR potentiator, VX-770. *Proc Natl Acad Sci USA* 106, 18825-18830 (2009).
4. Wainwright, C. E., et al. Lumacaftor-Ivacaftor in Patients with Cystic Fibrosis Homozygous for Phe508del CFTR. *N Engl J Med* (2015).
5. Nilius, B. & Droogmans, G. Amazing chloride channels: an overview. *Acta Physiol Scand* 177, 119-147 (2003).
6. Jia, L., Liu, W., Guan, L., Lu, M. & Wang, K. Inhibition of Calcium-Activated Chloride Channel ANO1/TMEM16A Suppresses Tumor Growth and Invasion in Human Lung Cancer. *PLoS One* 10, e0136584 (2015).
7. Stanich, J. E., et al. Ano1 as a regulator of proliferation. *Am J Physiol Gastrointest Liver Physiol* 301, G1044-1051 (2011).
8. Ruffin, M., et al. Anoctamin 1 dysregulation alters bronchial epithelial repair in cystic fibrosis. *Biochim Biophys Acta* 1832, 2340-2351 (2013).
9. Sonneville, F., et al. New Insights about miRNAs in Cystic Fibrosis. *Am J Pathol* (2015).
10. Bonvin, E., et al. Congenital tracheal malformation in cystic fibrosis transmembrane conductance regulator-deficient mice. *J Physiol* 586, 3231-3243 (2008).
11. Galietta, L. J., et al. IL-4 is a potent modulator of ion transport in the human bronchial epithelium in vitro. *J Immunol* 168, 839-845 (2002).
12. Caputo, A., et al. TMEM16A, a membrane protein associated with calcium-dependent chloride channel activity. *Science* 322, 590-594 (2008).
13. Knowles, M. R., Clarke, L. L. & Boucher, R. C. Activation by extracellular nucleotides of chloride secretion in the airway epithelia of patients with cystic fibrosis. *N Engl J Med* 325, 533-538 (1991).
14. Lazarowski, E. R. & Boucher, R. C. Purinergic receptors in airway epithelia. *Curr Opin Pharmacol* 9, 262-267 (2009).
15. Kellerman, D., Evans, R., Mathews, D. & Shaffer, C. Inhaled P2Y2 receptor agonists as a treatment for patients with Cystic Fibrosis lung disease. *Adv Drug Deliv Rev* 54, 1463-1474 (2002).
16. Kunzelmann, K., et al. Purinergic inhibition of the epithelial Na+ transport via hydrolysis of PIP2. *FASEB J* 19, 142-143 (2005).
17. Yerxa, B. R., et al. Pharmacology of INS37217 [P(1)-(uridine 5')-P(4)-(2'-deoxycytidine 5')tetraphosphate, tetrasodium salt], a next-generation P2Y(2) receptor agonist for the treatment of cystic fibrosis. *J Pharmacol Exp Ther* 302, 871-880 (2002).

18. Moss, R. B. Pitfalls of drug development: lessons learned from trials of denufosol in cystic fibrosis. *J Pediatr* 162, 676-680 (2013).
19. D J, K., M, M.-W. & C, J. Pharmacokinetics of INS37217 after inhaled and intravenous administration in healthy volunteers. in *Pediatr Pulmonol* Vol. 38 (Suppl. 27) 348 (North American cystic fibrosis conference, 2004).
20. Saiman, L., et al. Effect of azithromycin on pulmonary function in patients with cystic fibrosis uninfected with *Pseudomonas aeruginosa*: a randomized controlled trial. *Jama* 303, 1707-1715 (2010).
21. Quan, J. M., et al. A two-year randomized, placebo-controlled trial of dornase alfa in young patients with cystic fibrosis with mild lung function abnormalities. *J Pediatr* 139, 813-820 (2001).
22. Chung, A. C., Yu, X. & Lan, H. Y. MicroRNA and nephropathy: emerging concepts. *International journal of nephrology and renovascular disease* 6, 169-179 (2013).
23. Yu, L., et al. Early detection of lung adenocarcinoma in sputum by a panel of microRNA markers. *Int J Cancer* 127, 2870-2878 (2010).
24. Kurreck, J., Wyszko, E., Gillen, C. & Erdmann, V. A. Design of antisense oligonucleotides stabilized by locked nucleic acids. *Nucleic Acids Res* 30, 1911-1918 (2002).
25. Lennox, K. A. & Behlke, M. A. A direct comparison of anti-microRNA oligonucleotide potency. *Pharm Res* 27, 1788-1799 (2010).
26. Janssen, H. L., et al. Treatment of HCV infection by targeting microRNA. *N Engl J Med* 368, 1685-1694 (2013).

The invention claimed is:

1. A method of treating cystic fibrosis in a subject in need thereof comprising administering to the subject a therapeutically effective amount of a nucleic acid miR-9 inhibitor comprising the nucleic acid sequence of SEQ ID NO: 3, wherein the nucleic acid miR-9 inhibitor does not bind directly to miR-9 but instead binds to a miR-9 mRNA target site in an anoctamin-1 (ANO1) nucleic acid sequence.

2. The method of claim 1 wherein the miR-9 mRNA target site is located on a ANO1 3'UTR.

3. The method of claim 1 wherein the nucleic acid miR-9 inhibitor is a Target Site Blocker (TSB).

4. The method of claim 1 wherein the nucleic acid miR-9 inhibitor comprises LNA nucleotides, or morpholino nucleotides, or 2'-O-methyl modified nucleotides, or 2'-O-methoxyethyl modified nucleotides, or 2'-fluro modified nucleotides.

5. The method of claim 1 wherein the nucleic acid miR-9 inhibitor is delivered using a viral vector.

6. The method of claim 5 wherein the vector is an AAV vector.

7. The method of claim 1 wherein the nucleic acid miR-9 inhibitor is administered to the subject using a method that enables the nucleic acid miR-9 inhibitor to reach the lungs.

8. A viral vector encoding a nucleic acid miR-9 inhibitor comprising the sequence of SEQ ID NO: 3 wherein the nucleic acid miR-9 inhibitor is not configured to bind directly to miR-9 but instead is configured to bind to a miR-9 mRNA target site in an anoctamin-1 (ANO1) nucleic acid sequence.

9. A composition comprising a viral vector encoding a nucleic acid miR-9 inhibitor comprising the sequence of SEQ ID NO: 3 wherein the nucleic acid miR-9 inhibitor is not configured to bind directly to miR-9 but instead is configured to bind to a miR-9 mRNA target site in an anoctamin-1 (ANO1) nucleic acid sequence; and a pharmaceutically acceptable carrier.

* * * * *